(12) United States Patent
Vescovi et al.

(10) Patent No.: US 9,220,756 B2
(45) Date of Patent: Dec. 29, 2015

(54) INHIBITION OF THE TUMORIGENIC POTENTIAL OF TUMOR STEM CELLS BY LIF AND BMPS

(75) Inventors: Angelo Luigi Vescovi, Pescone (IT); Brent Allen Reynolds, Parksville (CA)

(73) Assignee: STEMGEN S.P.A., Milan (IT)

( * ) Notice: Subject to any disclaimer, the term of this patent is extended or adjusted under 35 U.S.C. 154(b) by 1399 days.

(21) Appl. No.: 11/996,214

(22) PCT Filed: Jul. 19, 2006

(86) PCT No.: PCT/IB2006/002296
§ 371 (c)(1),
(2), (4) Date: Mar. 9, 2010

(87) PCT Pub. No.: WO2007/010394
PCT Pub. Date: Jan. 25, 2007

(65) Prior Publication Data
US 2010/0167999 A1    Jul. 1, 2010

Related U.S. Application Data

(60) Provisional application No. 60/700,859, filed on Jul. 19, 2005.

(51) Int. Cl.
*A61K 38/16* (2006.01)
*A61K 38/17* (2006.01)
*A61K 38/18* (2006.01)
*A61K 38/20* (2006.01)

(52) U.S. Cl.
CPC ......... *A61K 38/1875* (2013.01); *A61K 38/2093* (2013.01)

(58) Field of Classification Search
None
See application file for complete search history.

(56) References Cited

U.S. PATENT DOCUMENTS

| 5,863,738 | A * | 1/1999 | Dijke et al. ................... 435/7.1 |
| 6,429,224 | B1 * | 8/2002 | Calabresi et al. ............. 514/422 |
| 2007/0203329 | A1 * | 8/2007 | Miyazono et al. ............ 530/350 |
| 2010/0015150 | A1 * | 1/2010 | Carlson et al. ............. 424/139.1 |

FOREIGN PATENT DOCUMENTS

| WO | WO 91/13985 | 9/1991 |
| WO | WO 00/29012 | 5/2005 |
| WO | WO 2005/057172 A2 | 6/2005 |

OTHER PUBLICATIONS

Sell (2004, Crit. Rev. Oncol./Hematol. 51:1-28).*
Al-Hajj et al. (2003, PNAS USA 100:3983-3988).*
Reya et al. (2001, Nature 414:105-111).*
Piccirillo, S. G. M. et al., "Bone morphogenetic proteins inhibit the tumorigenic potential of human brain tumour-initiating cells," Nature, Dec. 7, 2006, vol. 444, No. 7120, pp. 761-765.
Ro Torstein Baade et al: "Bone morphogenetic protein −5, −6 and −7 inhibit growth and induce apoptosis in human myeloma cells", Oncogene, vol. 23, No. 17, Apr. 15, 2004, pp. 3024-3032.
Soda H et al: "Antiproliferative Effects of Recombinant Human Bone Morphogenetic Protein-2 on Human Tumor Colony-Forming Units", Anti-Cancer Drugs, Rapid Communications, Oxford, GB, vol. 9, No. 4, Apr. 1998, pp. 327-331.
Andrews P W et al: "Inhibition of Proliferation and Induction of Differentiation of Pluripotent Human Embryonal Carcinoma Cells by Osteogenic Protein-1(or Bone Morphogenetic Protein-7), Laboratory Osteogenic Protein-1(or Bone Morphogenetic Protein-7)", Laboratory Investigation, United States and Canadian Academy of Pathology, Baltimore, US, vol. 71, No. 2, 1994, pp. 243-251.
Ying Qi-Long et al: "BMP induction of Id proteins suppresses differentiation and sustains embryonic stem cell self-renewal in collaboration with STAT3", CELL, vol. 115, No. 3, Oct. 31, 2003, pp. 281-292.
Galli Rossella et al: "Isolation and characterization of tumorigenic, stem-like neural precursors from human glioblastoma", Cancer Research, vol. 64, No. 19, Oct. 1, 2004, pp. 7011-7021.
Liu J et al: "Expression of leukemia-inhibitory factor as an autocrinal growth factor in humanmedulloblastomas", Journal of Cancer Research and Clinical Oncology, Springer International, Berlin, DE, vol. 125, No. 8-9, Aug. 1999, pp. 475-480 -& Database Medline [Online]US National Library of Medicine (NLM), Bethesda, MD, US; Apr. 1991, Valtz N L El Al: "An embryonic origin for medulloblastoma" -& The New Biologist Apr 1991, vol. 3, No. 4, Apr. 1991, pp. 364-371.
Estrov Z et al: "Leukemia Inhibitory Factor Binds to Human Breast Cancer Cells and Stimulates Their Proliferation", Journal of Interferon and Cytokine Research, Mary Ann Liebert, New York, NY, US, vol. 15, No. 10, Oct. 1995, pp. 905-913.
Lumniczky Katalin et al: "Local tumor irradiation augments the antitumor effect of cytokine-producing autologous cancer cell vaccines in a murine glioma model", Cancer Gene Therapy, vol. 9, No. 1, Jan. 2002, pp. 44-52.

(Continued)

Primary Examiner — Elizabeth C Kemmerer
(74) Attorney, Agent, or Firm — Chiesa Shahinian & Giantomasi PC

(57) ABSTRACT

The present disclosure includes methods and compositions for the treatment or prevention of diseases and disorders characterized by excessive or misregulated cellular proliferations, including methods for the treatment of tumors. The methods involve the use of pharmaceutical compositions comprising at least one agent selected from the group consisting of a LIF preparation, a BMP preparation, a BMPR signalling activator, and a LIFR signalling activator. The disclosure also includes LIF preparations, BMP preparations, BMPR signalling activator, and LIFR signalling activators, and methods for the identification of LIF preparations, BMP preparations, BMPR signalling activator, and LIFR signalling activators. The disclosure also includes pharmaceutical compositions comprising at least one agent selected from the group consisting of a LIF preparation, a BMP preparation, a BMPR signalling activator, and a LIFR signalling activator.

13 Claims, 17 Drawing Sheets

(56) References Cited

OTHER PUBLICATIONS

Liu Houqi et al: "Molecular analysis of signaling events mediated by the cytoplasmic domain of leukemia inhibitory factor receptor alpha subunit.", Molecular and Cellular Biochemistry Mar. 2004, vol. 258, No. 1-2, Mar. 2004, pp. 15-23.
He W et al: "Membrane distal cytokine binding domain of LIFR interacts with soluble CNTFR in vitro", FEBS Letters, Elsevier, Amsterdam, NL, vol. 514, No. 2-3, Mar. 13, 2002, pp. 214-218.
Ficcirillo S G M et al: "Bone morphogenetic proteins inhibit the tumorigenic potential of human brain tumour-initiating cells", Nature Dec. 7, 2006, vol. 444, No. 7120, Dec. 7, 2006, pp. 761-765.
Gilbertson. R. J., "Resolving the stem-cell debate," Nature, 488: 462 (2012).
Graham, T. A., "Stemming tumour evolution," Nature, 488: 463 (2012).
Chen, J. et al., "A restricted cell population propagates glioblastoma growth after chemotherapy," Nature, 488: 522-526 (2012).
Driessens, G. et al., "Defining the mode of tumour growth by clonal analysis," Nature, 488: 527-531 (2012).
Iantosca, M. R. et al., "Bone morphogenetic proteins-2 and -4 attenuate apoptosis in a cerebellar primitive neuroectodermal tumour cell line," Journal of Neuroscience Research, 56: 248-258 (1999).
Shon SK, et al. "Bone morphogenetic protein-4 induced by NDRG2 expression inhibits MMP-9 activity in breast cancer cells." Biochem Biophys Res Commun. 2009; 385(2): 198-203.
Ketolainen JM, et al. "Parallel inhibition of cell growth and induction of cell migration and invasion in breast cancer cells by bone morphogenetic protein 4." Breast Cancer Res Treat. 2010; 124(2): 377-86.
Deng H, et al. "Bone morphogenetic protein-4 is overexpressed in colonic adenocarcinomas and promotes migration and invasion of HCT116 cells." Exp Cell Res. 2007; 313(5): 1033-44.
Buckley S, et al. "BMP4 signaling induces senescence and modulates the oncogenic phenotype of A549 lung adenocarcinoma cells." Am J Physiol Lung Cell Mol Physiol. 2004; 286(1): L81-6.
Kallioniemi A. "Bone morphogenetic protein 4-a fascinating regulator of cancer cell behavior." Cancer Genet. 2012; 205(6): 267-77.
Zhou Z, et al. "Bone morphogenetic protein 4 inhibits cell proliferation and induces apoptosis in glioma stem cells." Cancer Biother Radiopharm. 2011; 26(1): 77-83.
Xu RH, et al. "Basic FGF and suppression of BMP signaling sustain undifferentiated proliferation of human ES cells." Nat Methods. 2005; 2(3): 185-90.
Yang Y, et al. "Heightened potency of human pluripotent stem cell lines created by transient BMP4 exposure." Proc Natl Acad Sci USA. 2015; 112(18): E2337-46.
Panchision DM, et al. "Sequential actions of BMP receptors control neural precursor cell production and fate." Genes Dev. 2001; 15(16): 2094-1110.
Binda E, et al. "Glioma stem cells: turpis omen in nomen? (The evil in the name?)." J Intern Med. 2014; 274(1): 25-40.
Halfter H., et al. "Growth inhibition of newly established human glioma cell lines by leukemia inhibitory factor." J Neurooncol. Aug. 1998; 39(1): 1-18.

\* cited by examiner

A

B

A

B

INHIBITION OF THE TUMORIGENIC POTENTIAL OF TUMOR STEM CELLS BY LIF AND BMPS

This application is the 371 National Stage of International Application No. PCT/IB2006/02296, filed Jul. 19, 2006, which claims the benefit of U.S. Provisional Patent Application Ser. No. 60/700,859, filed Jul. 19, 2005, the contents of each of which are incorporated herein by reference in their entirety.

BACKGROUND OF THE INVENTION

Reference to any prior art in this specification is not, and should not be taken as, an acknowledgment or any form of suggestion that this prior art forms part of the common general knowledge in any country. All references cited herein are specifically incorporated herein by reference in their entirety.

Neural Stem Cells

Traditionally, stem cells were thought to be located only in tissues where differentiated cells were most susceptible to loss and the need for replacement great, such as the skin (Huelsken et al., Cell 105: 533-45, 2001), intestinal epithelia (Potten et al., Development 110: 1001-20, 1990) and the blood (Morrison et al., Annu Rev Cell Dev Biol 11: 35-71, 1995). Indeed, the best-known example of an adult stem cell is the hematopoietic stem cell (HSC), which is found in the bone marrow and is ultimately responsible for the generation of all blood cell types throughout the life of the animal (Morrison et al., supra.; Weissman, Cell 100: 157-68, 2000; Weissman, Science 287: 1442-6, 2000). Since the adult central nervous system (CNS) was thought not to exhibit a significant amount of neuronal death, and have no regenerative capacity, the existence of neural stem cells seemed both unlikely, and unnecessary. However, in 1992 two independent groups successfully demonstrated the existence of precursor cells within the adult mammalian CNS with the ability to give rise to new neurons (Reynolds and Weiss, Science 255: 1707-10, 1992; Richards et al., Proc Natl Acad Sci USA 89: 8591-5, 1992).

The source of the new neurons was identified as stem cells that line the entire ventricular neuroaxis of the adult mammalian CNS (Reynolds and Weiss, 1992). Like stem cells found in other tissues, CNS stem cells (or neural stem cells (NSCs)) have been shown to demonstrate the defining in vitro stem cell characteristics (Hall et al., Development 106: 619-33, 1989; Potten et al, supra.) of proliferation, extensive self-renewal, generation of a large number of progeny, multi-lineage differentiation potential and the in vivo characteristic of regenerating tissue after injury.

One of the roles of a stem cell is to divide and give rise to more committed precursor cells with the ability to proliferate and generate a large number of undifferentiated cells. Ultimately it is the progeny of these more committed precursor cell types that give rise to differentiated progeny. Thus, stem cells can be thought of as a relatively quiescent reservoir of uncommitted cells with the ability to divide throughout the lifespan of the animal and hence with an extensive proliferation potential, while progenitor cells are more committed and divide more frequently but have a more limited proliferation potential over time. Both during development, and in the adult, the proliferation of stem and progenitor cells underpins cell genesis.

Due to the lack of any specific morphological, molecular or antigenic signature stem cells are identified based on a functional criterion. Hence, to study the regulation of stem cells in vitro a tissue culture methodology must be developed that induces stem cell division. Few such assays exist, however, in the nervous system a culture methodology referred to as the Neurosphere Assay (NA) (Reynolds and Weiss, supra.) is commonly used to identify, propagate and enumerate NSCs in vitro. Briefly, the NA involves the microdissection of embryonic through to adult CNS tissue followed by the disruption of cell to cell contacts and the generation of a suspension of single cells. Cells are plated (typically at a low density) in tissue cultureware in a defined serum-free medium in the presence of at least one proliferation-inducing growth factor (i.e. Epidermal Growth Factor [EGF], basic Fibroblastic Growth Factor [bFGF] etc.). Under these conditions within 2-5 days a multipotent NSC begins to divide giving rise to a clonally derived cluster of undifferentiated cells referred to as a neurosphere. In the continued presence of the proliferation inducing factor the cells in the neurosphere continue to divide resulting in an increase in the number of cells comprising the neurosphere and consequently the size of the neurosphere. Neurospheres can be collected, disrupted in to a single cell suspension, and the cells replated in culture to generate new neurospheres. Passaging of NSC in this manner results in an arithmetic increase in viable CNS precursor cells. The NA assay allows for NSCs to be isolated and expanded in defined conditions so the behavior of the putative stem cells can be studied under different experimental conditions. The NA has become the standard assay for the isolation of mammalian NSC and forms the core of many assays used to understand the cellular and molecular biology of stem cells in the nervous system.

The concept of tumors arising from a small population of cells with stem cell characteristics that contribute to the growth and propagation of the tumor is not new to the cancer biology field. The idea was proposed in early 1970's and experimentally confirmed in studies on acute myelogenousleukaemia (AML) where low frequency tumor initiating cells were demonstrated to resemble normal haematopoietic stem cells (HSCs). These studies suggested that leukemia stem cells were the direct descendents of HSC or the produce of a more differentiated cell that had acquired HSC features. Discovery of stem cells outside of the blood system raised the possibility that cancers of solid tissues may also contain stem like cells. The existence and isolation of tumor initiating stem-like cells in solid tumors was first demonstrated in human breast cancer tissue, an approach that has also been applied to tumors of the CNS.

Several groups have recently reported on the ability of cells derived from human glioma tissue to generate neurosphere-like cells in culture, suggesting the presence of NSCs within CNS tumors. Interestingly, it has been demonstrated, based on fluorescence activated cell sorting (FACS) isolation of "side-population" cells, that the well-established C6 glioma cell line contains a minor population of neurosphere-forming cells that retain in vivo malignancy. Galli and colleagues (Galli et al., Cancer Research (2004) 64: 7011-7021) reported on the isolation, propagation and serial transplantation of tumor neural stem cells (tNSCs) from human glioblastoma multiforme (GBM) that exhibit near identical functional properties as NSC derived from the embryonic and adult CNS. These GBM tNSCs are prominin positive precursors, which display the critical neural stem cell features in vitro, can be expanded in a stable fashion and, throughout serial transplantation-culturing cycles reproduce the original tumor-initiating characteristics. Together, these studies strongly support the hypothesis that CNS tumors contain a population of stem cells that may be responsible for tumor initiation and malignancy. The tNSCs can be sorted from other GBM cells using FACS by virtue of the expression on the tNSCs of CD133 (Singh et al., Nature (2004) 432:396-401).

GBM is the most common adult malignant brain tumor, with a median survival time of 9-12 months. The vast majority of patients die by two years from diagnosis. There is essentially no cure, and management therapy is commonly based on the combination of surgery, radiotherapy and chemotherapy. Survival rates have changed very little in over thirty years, which has prompted the active search for new treatments such as gene therapy, antiangiogenesis, immunotherapy and small molecule transduction inhibitors.

LIF

Leukemia inhibitory factor (LIF) is a polyfunctional glycoprotein cytokine whose inducible production can occur in many, perhaps all, tissues. LIF is also sometimes referred to as Cholinergic Differentiation Factor (CDF). LIF acts on responding cells by binding to a heterodimeric membrane receptor composed of a low-affinity LIF-specific receptor (LIFR) and the gp130 receptor chain also used as the receptor for interleukin-6, oncostatin M, cardiotrophin-1, and ciliary neurotrophic factor. LIF is essential for blastocyst implantation and the normal development of hippocampal and olfactory receptor neurons. LIF is used extensively in experimental biology because of its key ability to induce embryonic stem cells to retain their totipotentiality. LIF has a wide array of actions, including acting as a stimulus for platelet formation, proliferation of some hematopoietic cells, bone formation, adipocyte lipid transport, adrenocorticotropic hormone production, neuronal survival and formation, muscle satellite cell proliferation, and acute phase production by hepatocytes (for review see Metacalf, Stem Cells 2003; 21:5-14).

BMP

Bone morphogenetic proteins (BMPs) are members of the TGF-h superfamily (Hoodless et al., Cell 85:489-500, 1996). There are more than 20 members known that can be sub-grouped according to the homology in their sequence (Hoodless et al., supra, Wozney et al. J Cell Sci, Suppl 13:149-156, 1990). BMPs play crucial roles during the embryonic development. For example, they influence gastrulation, neurogenesis, apoptosis and hematopoiesis (see Nohe et al., Cellular Signalling 16, 291-299 (2004) for review). BMP receptors are hereinafter referred to as BMPRs. BMPRs from humans include BMPR1a, BMPR1b, and BMPR2.

In accordance with the present disclosure, it has now been determined that LIF and BMPs regulate progenitor and stem cell survival, self-renewal, proliferation and/or differentiation and in particular can reduce the numbers of proliferating cells in cancerous tissues.

SUMMARY OF THE INVENTION

In one aspect, the disclosure provides methods for the treatment or prevention of a disease or disorder characterized by excessive or misregulated cellular proliferation. The methods comprise administering a therapeutically effective amount of a Leukemia inhibitory factor (LIF) preparation and/or at least one Bone Morphogenetic Protein (BMP) preparation to a subject or tissue thought to be undergoing such excessive or misregulated cellular proliferation.

In another aspect the disclosure provides a method for reducing the growth of a tumor comprising administering a therapeutically effective amount of a Leukemia inhibitory factor (LIF) preparation and/or a Bone Morphogenetic Protein (BMP) preparation to said tumor. Included is a method for reducing the growth of a tumor in a human patient, including brain tumors (for example, glioblastoma multiforme) by administering a BMP-4 preparation to a human patient.

In a further aspect, the disclosure provides a method of decreasing the number of tumor stem cells and/or tumor progenitor cells in a tumor comprising contacting the tumor with a LIF preparation and/or a BMP preparation.

In another aspect, the disclosure provides LIF preparations and BMP preparations which are capable of increasing LIF receptor (LIFR) mediated signalling or BMP receptor (BMPR) mediated signalling, respectively, in a tumor stem cell or a tumor progenitor cell.

In another aspect, the present disclosure provides agents, hereinafter referred to as "LIFR signalling activators" and "LIF Receptor signalling activators" which are capable of increasing LIF receptor (LIFR)-mediated signalling in a tumor stem cell or tumor progenitor cell.

In another aspect the disclosure provides a method of reducing the growth of a tumor by increasing LIFR or BMPR-mediated signalling in said tumor. LIFR mediated signalling may be activated, for example, using a LIF preparation and/or a LIFR signalling activator; BMPR mediated signalling may be activated, for example, using a BMP preparation and/or a BMPR signalling activator.

In another aspect, the disclosure provides methods for the identification of LIFR signalling activators and BMPR signalling activators.

In another aspect, the disclosure provides methods for the treatment or prevention of a disease or disorder characterized by excessive or misregulated cellular proliferation. The methods involve administering a therapeutically effective amount of LIFR signalling activator and/or BMPR signalling activator to a subject or tissue thought to be undergoing such excessive or misregulated cellular proliferation.

In another aspect, the disclosure provides a method of decreasing the number of tumor stem cells and/or tumor progenitor cells in a tumor comprising contacting the tumor with a LIFR signalling activator and/or a BMPR signalling activator.

In another aspect the disclosure provides a method for reducing the growth of a tumor comprising administering a therapeutically effective amount of a LIFR signalling activator and/or a BMPR signalling activator to said tumor.

In another aspect, the disclosure provides methods for reducing the likelihood that a tumor stem cell or tumor progenitor cell undergoes a symmetrical division, the method comprising contacting the tumor stem cell or tumor progenitor cell with at least one agent selected from the group consisting of a LIF preparation, a BMP preparation, a BMPR signalling activator, and a LIFR signalling activator.

In another aspect, the disclosure provides methods for reducing neural stem cell frequency and neural progenitor cell frequency in serially passaged neural stem cells comprising contacting the neural stem cells with a LIF preparation and/or a BMP preparation.

In another aspect, the disclosure provides pharmaceutical compositions comprising at least one agent selected from the group consisting of a LIF preparation, a BMP preparation, a BMPR signalling activator, and a LIFR signalling activator.

In a further aspect, the use of BMP or LIF preparation in the manufacture of a medicament for the treatment of a tumor is disclosed, including use of a BMP-4 preparation in the manufacture of a medicament for the therapeutic and/or prophylactic treatment of brain tumors (for example, glioblastoma multiforme).

In a further aspect, the disclosure provides methods for the treatment of tumors that comprise tumor stem cells, comprising contacting the tumor stem cells with an agent that induces differentiation of the tumor stem cells. Suitable differentiating agents include LIF preparations, BMP preparations, BMPR signalling activators, and LIFR signalling activators. For example, a glioblastoma multiforme may be treated according to the methods of the disclosure by contacting tumor neural stem cells in the tumor (or remaining in the resection cavity following surgical de-bulking of the tumor) with a BMP-4 preparation in an amount sufficient to induce differentiation of the tumor neural stem cells.

BRIEF DESCRIPTION OF THE FIGURES

FIG. 14A shows a tumor mass in mice injected with untreated GBM cells. FIG. 14B shows the absence of a comparable tumor mass in mice injected with BMP-4 treated GBM cells. FIG. 14C shows tumors in mice co-treated with control beads that lack BMP-4. FIG. 14D shows the absence of comparable tumors in mice co-treated with BMP-4 beads. FIG. 14F shows the absence of comparable tumors in mice post-treated with BMP-4 beads. FIG. 14G shows the cellular morphology of untreated GBM tumors in mice. FIG. 14H shows the cellular morphology of BMP-4 treated GBM tumors in mice. FIG. 14J shows survival graphs for GBM injected mice treated pre- (left panel), co- (centre panel) and post- (right panel) GBM injection with either control beads or BMP-4 beads.

DETAILED DESCRIPTION OF THE PREFERRED EMBODIMENTS

Figure 1:
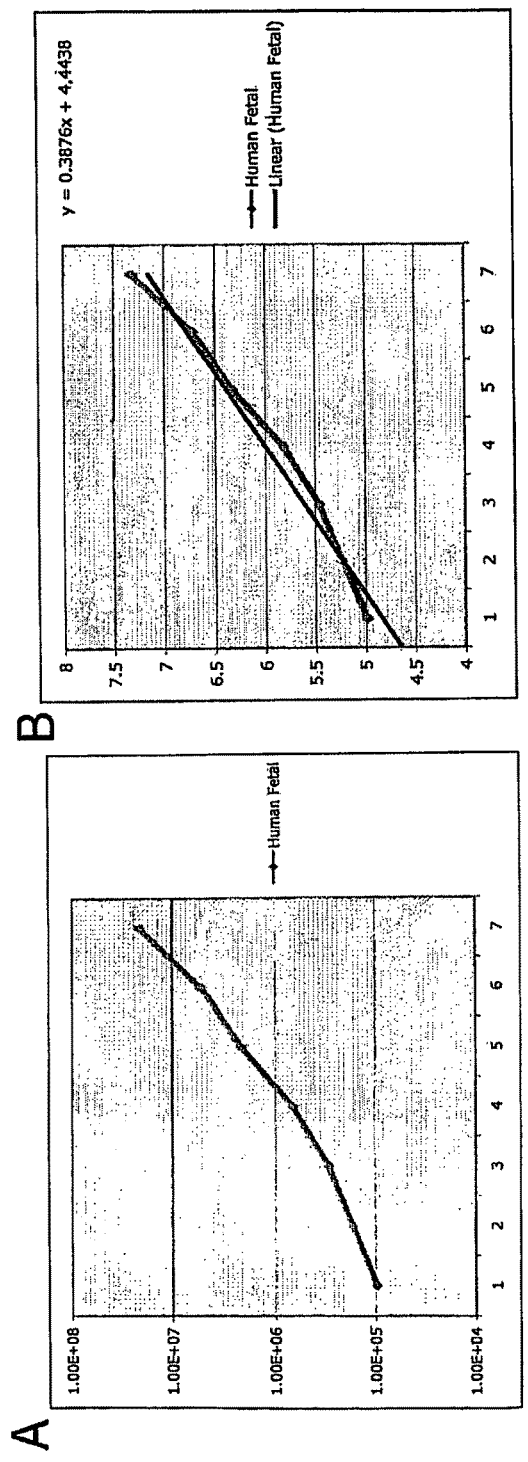
FIG. 1A shows a plot of the theoretical total number of cells at the end of each passage vs. passage number for human neural stem cells.
FIG. 1B shows the log of the total number of cells at the end of each passage vs. passage number and a best-fit trend line for the linear log plot.

Prior to describing the present disclosure in detail, it is to be understood that unless otherwise indicated, the subject disclosure is not limited to specific formulation components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to a "agent" includes a single agent, as well as two or more agents; reference to a "stem cell" includes a single stem cell, as well as two or more stem cells; and so forth.

As used herein, a "therapeutically effective amount" refers to that amount of a therapeutic agent sufficient to treat or manage a disease or disorder characterized by excessive or misregulated cellular proliferation and, preferably, the amount sufficient to destroy, modify, control or remove primary, regional or metastatic cancer tissue. A therapeutically effective amount may refer to the amount of therapeutic agent sufficient to delay or minimize the onset of the disease or disorder characterized by excessive or misregulated cellular proliferation, e.g., delay or minimize the spread of cancer or the growth of a tumor. A therapeutically effective amount may also refer to the amount of the therapeutic agent that provides a therapeutic benefit in the treatment or management of a tumor or of cancer. Further, a therapeutically effective amount with respect to a therapeutic agent of the disclosure means that amount of therapeutic agent alone, or in combination with other therapies, that provides a therapeutic benefit in the treatment or management of hyperproliferative cell disease or cancer. The term can encompass an amount that improves overall therapy, reduces or avoids unwanted effects, or enhances the therapeutic efficacy of or synergies with another therapeutic agent.

The terms "agent", "compound", "active agent", "active compound," "therapeutic agent," "pharmacologically active agent", "medicament", "active" and "drug" are used interchangeably herein to refer to a substance that induces a desired pharmacological and/or physiological effect. The terms also encompass pharmaceutically acceptable and pharmacologically active ingredients of those active agents specifically mentioned herein including but not limited to salts, esters, amides, prodrugs, active metabolites, analogs and the like. When the terms "agent", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. The agents of the present disclosure may be any proteinaceous molecules such as peptides, polypeptides and proteins or non-proteinaceous molecules such as nucleic acid molecules and small to large natural or synthetically derived organic and inorganic molecules. The agents can generally cross the blood-brain barrier or may be suitable for direct administration to the CNS.

Reference herein to "treatment" may mean a reduction in the severity of an existing disease or condition. The term "treatment" is also taken to encompass "prophylactic treatment" to prevent the onset of a disease or condition. The term "treatment" does not necessarily imply that a subject is treated until total recovery. Similarly, "prophylactic treatment" does not necessarily mean that the subject will not eventually contract a disease or condition.

"Stem cell" as used herein refers to an undifferentiated cell capable of, (a) proliferation, (b) self renewal over an extended period of time, (c) able to generate a large number of progeny, and (d) the ability to give rise to all the cell types of the tissue from which it is obtained.

As used herein, a "tumor stem cell" is a stem cell obtained from a tumor. A tumor stem cell is capable of (a) proliferation, (b) self renewal over an extended period of time, (c) able to generate a large number of progeny, and (d) the ability to give rise to all the cell types of the tumor from which it is obtained. A "tumor neural stem cell," also referred to herein as a "tNSC," refers to tumor stem cell obtained from a tumor of the CNS.

"Progenitor cell" as used herein refers to an undifferentiated cell capable of, (a) proliferation, (b) limited self renewal ability, (c) generation of a limited number of progeny and (d) the ability to give rise to at least one type of progeny.

As used herein, a "tumor progenitor cell" is a progenitor cell obtained from a tumor. A tumor progenitor cell is capable of (a) proliferation, (b) limited self renewal ability, (c) generation of a limited number of progeny and (d) the ability to give rise to at least one cell type found in the tumor from which it is obtained.

LIF Preparations and BMP Preparations

In one aspect, the disclosure provides methods for the treatment or prevention of a disease or disorder characterized by excessive or misregulated cellular proliferation. The methods comprise administering a therapeutically effective amount of a Leukemia inhibitory factor (LIF) preparation and/or at least one Bone Morphogenetic Protein (BMP) preparation to a subject or tissue thought to be undergoing such excessive or misregulated cellular proliferation.

Preferably the disorder characterized by excessive proliferation is a benign tumor or a malignant tumor (cancer). For example, the tumor may be a brain tumor including, but not limited to, acoustic neuroma, adenoma, astrocytoma, juvenile pilocytic astrocytoma, brain stem glioma, chordoma, choroid plexus, craniopharyngioma, ependymoma, ganglioglioma, ganglioglioneurocytoma, glioblastoma multiforme (GBM), glioma, lymphoma, medulloblastoma, meningioma, oligodendroglioma, optic nerve glioma, pituitary tumors, pineal tumors, or pineoblastoma. In preferred embodiments, the brain tumor is GBM.

In another aspect the disclosure provides a method for reducing the growth of a tumor comprising administering a therapeutically effective amount of a Leukemia inhibitory factor (LIF) preparation and/or at least one Bone Morphogenetic Protein (BMP) preparation to said tumor. In some embodiments, a therapeutically effective amount of a BMP-4 preparation is administered to GBM in a human patient in order to reduce the growth of the GBM.

In a further aspect, the disclosure provides a method of decreasing the number of tumor stem cells and/or tumor progenitor cells in a tumor comprising contacting the tumor with a LIF preparation and/or a BMP preparation. Without being limited by theory or hypothesis, it is believed that when administered to a tumor, LIF preparations and BMP preparations lead to an increase in LIFR or BMPR-mediated signalling, which results in the modulation of any one or more of the following tumor stem cell or tumor progenitor cell properties such as, but not limited to, cell survival, self-renewal, symmetric division, proliferation and/or differentiation properties. In particular, and without being limited by theory or hypothesis, it is believed that the increase in LIFR or BMPR-mediated signalling results in a reduction in the proliferation properties of stem and progenitor cells and in particular a reduction in the probability of symmetric division exhibited by proliferating stem cells or progenitor cell thereby reducing their numbers. Accordingly, in another aspect the disclosure provides a method for reducing the likelihood that a tumor stem cell or tumor progenitor cell undergoes a symmetrical division, the method comprising contacting the tumor stem cell or tumor progenitor cell with a LIF preparation and/or a BMP preparation.

In another aspect the disclosure provides a method of reducing the growth of a tumor by increasing LIFR or BMPR-mediated signalling in said tumor. LIFR mediated signalling may be activated, for example, using a LIF preparation and/or a LIFR signalling activator (see below); BMPR mediated signalling may be activated, for example, using a BMP preparation and/or a BMPR signalling activator (see below).

Current treatments aimed at eradicating tumorigenic cells using conventional treatments are designed to eliminate rapidly cycling cells. For example, traditional chemotherapy agents are most effective against dividing cells. Like their non-transformed counterpart, tNSCs cycle infrequently and thereby escape the toxic effects of treatment and may easily re-initiate tumor expansion after treatment. The intrinsic longevity of adult stem cells and their inherent ability to express drug resistance and anti-apoptotic genes may be found in their malignant counterpart, compounding the difficulty in developing effective treatment strategies aimed at eradicating tumour stem cells. The methods and compositions disclosed herein overcome this difficulty by targeting the tNSC cells. Without being limited by theory or hypothesis, it is believed that the methods and compositions described herein have a pro-differentiation effect on tNSCs (as evidenced by the upregulation of neural differentiation markers, particularly astroglial antigens, as show in the Examples), and thus permanently reduce the stem cell pool without effecting cell viability or eliciting apoptosis. As a result (as shown in the Examples below), even a transient exposure to the compositions of the disclosure (particularly BMP-4 compositions for GBM treatment) irreversibly inhibits the tumorigenic potential of tNSCs.

Inducing differentiation of tumor cells, rather than trying to kill them, is an entirely new approach to cancer treatment. Thus, in another aspect the disclosure provides a method of treating a tumor comprising tumor stem cells, the method comprising contacting the tumor stem cells with an agent (such as a BMP preparation) that induces their differentiation. In one such embodiment, tumor neural stem cells in a brain tumor, such as glioblastoma multiforme, are contacted with BMP-4 in order to induce their differentiation.

The terms "LIF preparation" and "BMP preparation" includes the LIF polypeptide or a BMP polypeptide as produced in nature, preferably in humans, with or without any post-translational modifications. This includes, for human LIF, the polypeptide encoded by the mRNA having the GenBank accession number NM__002309. For human BMPs, this includes the BMP polypeptides encoded by the human genes: BMP1, BMP2, BMP3, BMP4, BMP5, BMP6, BMP7, BMP8A, BMP8B, GDF10 (BMP-3b), GDF11 (BMP11), GDF2 (BMP9), BMP10, BMP15, and by the mRNAs having the GenBank accession numbers: NM 001719 (BMP7); NM__001201 (BMP3); NM__001200 (BMP2); NM__005448 (BMP15); NM__001720 (BMP8B); NM__014482 (BMP10); NM__006132 (BMP1-4); NM__006131 (BMP1-5); NM__006130 (BMP1-6); NM__006129 (BMP1-3): NM__006128 (BMP1-2): NM__001718 (BMP6); NM__001199 (BMP1-1); NM__130851 (BMP4-3); NM__130850 (BMP4-2); NM 001202 (BMP4-1); NM__181809 (BMP8A); NM 021073 (BMP5). Note that BMP-4 polypeptide is also sometimes referred to as BMP-2B.

Preferred BMPs for use in the methods and compositions of the disclosure include BMP-2, BMP-4, BMP-5, BMP-6, BMP-7, and BMP-8b. In particular, exposure to BMP-4 is shown in the Examples below to enforce the maturation of cells isolated from human GBM while not affecting overall viability and apoptosis. This results in the upregulation of neuronal and glial markers and also results in a major reduction in proliferation ability. BMP-4 exposure—even transiently—is shown in the Examples below to greatly reduce the size of GBM tNSCs populations (CD133+ GBM cells) in GBM cultures, to greatly reduce the clonogenic index of GBM cells, and to dramatically reduce the kinetics of expansion of GBM tNSCs. These effects are irreversible and extinguish the in vivo tumour-initiating ability of human GBM cells.

The term "LIF preparation" or "BMP preparation" as used herein also includes fragments of LIF or BMP polypeptides or glycopolypeptides which at least partially retain the ability to attenuate excessive cellular proliferation in the assays and treatment methods of the disclosure e.g. which retain between 1-100% of the activity of full length LIF or a full length BMP in the assays or treatment methods of the disclosure. Such fragments may have increased activity relative to full length LIF or a full length BMP in the assays or treatment methods of the disclosure. Such fragments may have a continuous series of deleted residues from the amino or the carboxy terminus, or both, in comparison to the full length protein. The fragments may be characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, and substrate binding regions. The fragments may be produced by peptide synthesis techniques, or by cleavage of full length LIF or BMP polypeptide. The fragments may be linked at their N termini, C termini, or both their N and C termini to other polypeptide sequences, thus forming fusion proteins.

The term "LIF preparation" or "BMP preparation" as used herein also includes a polypeptide or glycopolypeptide having an amino acid sequence which is partially homologous with the amino acid sequence of LIF or a BMP polypeptide, or a fragment thereof, as disclosed above, and which at least partially retain the ability to attenuate excessive cellular proliferation in the assays and treatment methods of the disclosure. Homologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to LIF or BMP, or fragments thereof.

The term "LIF preparation" or "BMP preparation" also includes variants of LIF or BMP full length polypeptide, and variants of LIP or BMP fragments. Such variants at least partially retain the ability to attenuate excessive cellular proliferation in the assays and treatment methods of the disclosure. Variants may include deletions, insertions, inversions, repeats, and substitutions selected according to general rules known in the art so as have little effect on activity. For example, guidance concerning how to make phenotypically silent amino acid substitutions is provided in Bowie et al., Science 247: 1306-1310 (1990), incorporated by reference herein in its entirety. For example, variants can be obtained by site directed mutagenesis or alanine-scanning mutagenesis (introduction of single alanine mutations at every residue in the molecule). (Cunningham and Wells, Science 244: 1081-1085 (1989). Variants may also have amino acid substitutions that contain, for example, one or more non-peptide bonds (which replace the peptide bonds) in the protein or peptide sequence. Variants may also have substitutions that include amino acid residues other than naturally occurring L-amino acids, e.g., D-amino acids or non-naturally occurring or synthetic amino acids, e.g., B or y amino acids. Variants may also include crosslinking groups which impose conformational constraints on the polypeptide. Variants may also include glycosylations, acetylations, phosphorylations and the like. Variants may also include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the LIF or BMP preparation (for example, polyethylene glycol), or to target the LIF or BMP preparation to a specific cell type (such as a tumor neural stem cell), or to allow the LIF or BMP preparation to cross the blood-brain barrier (BBB) and/or the blood-tumor barrier (BTB), or (iv) fusion of the polypeptide with additional amino acids or additional peptides or additional polypeptides, or (v) fusion to a cytoxic agent, for example to a toxin or radioactive compound, or (vi) fusion to a marker that may be used for imaging purposes, for example, a radiolabel.

The LIF preparations and BMP preparations of the disclosure can be prepared in any suitable manner, including through the isolation of naturally occurring polypeptides, by recombinant techniques, by polypeptide synthesis techniques, or by a combination of these methods. Methods for preparing such polypeptides are well understood in the art. The LIF or BMP preparations may be in the form of a larger protein, such as a fusion protein. It is often advantageous to include an additional amino acid sequence which contains secretory or leader sequences, pro-sequences, sequences which aid in purification, such as multiple histidine residues, or an additional sequence for stability during recombinant production.

The LIF preparations and BMP preparations of the present disclosure are preferably provided in an isolated form, and preferably are substantially purified. A recombinantly produced version of a LIF or BMP preparation can be substantially purified using techniques described herein or otherwise known in the art, such as, for example, by the one-step method described in Smith and Johnson, Gene 67: 31-40 (1988). LIF or BMP preparations of the disclosure also can be purified from natural, synthetic or recombinant sources using protocols known in the art, such as, for example, antibodies of the disclosure raised against the full-length LIF or BMP.

In some embodiments of the present disclosure a LIF preparation and/or BMP preparation may be administered to a subject directly such that endogenous tumor stem cells and tumor progenitor cells are regulated in vivo. For example, a BMP-4 preparation may be administered to a brain tumor, such as GBM, in a human patient. In alternative embodiments of the present disclosure, tumor stem cells and tumor progenitor cells may be contacted with the agents of the present disclosure in vitro. For example, an isolated tumor, which comprises tumor stem cells and tumor progenitor cells, may be contacted with the agents of the disclosure in vitro.

Methods for administering the LIF and/or BMP preparations to a subject, including to a tumor in a subject, along with pharmaceutical compositions comprising LIF and/or BMP preparations, are provided below in the section entitled "Administration and Pharmaceutical Compositions."

LIF Receptor Signalling Activators and BMP Receptor Signalling Activators

In another aspect embodiment, the present disclosure provides agents, hereinafter referred to as "LIFR signalling activators" and "LIF Receptor signalling activators" which are capable of increasing LIF receptor (LIFR)-mediated signalling in a tumor stem cell or tumor progenitor cell. The disclosure also provides methods for the identification of such LIFR signalling activators, and pharmaceutical compositions comprising such LIFR signalling activators. The LIFR signalling activators of the present disclosure may increase LIFR-mediated signalling in a stem or progenitor cell by activating LIFR directly (e.g. an agonist), or indirectly, such as by increasing the expression or activity of a secondary molecule or compound (e.g. by increasing expression of LIF itself, or by increasing the activity or expression a downstream component of LIFR-mediated signalling, such as JAK or STAT) in the tumor stem cell or tumor progenitor cell which in turn increases LIFR-mediated signalling in a tumor stem cell or tumor progenitor cell.

In an additional aspect, the present disclosure provides agents, hereinafter referred to as "BMPR signalling activators" and "BMP receptor signalling activators" which are capable of increasing BMP receptor (BMPR)-mediated signalling in a tumor stem cell or tumor progenitor cell. The disclosure also provides methods for the identification of such BMPR signalling activators, and pharmaceutical compositions comprising such BMPR signalling activators. The BMPR signalling activators of the present disclosure may increase BMPR-mediated signalling in a tumor stem cell or tumor progenitor cell by activating BMPR directly (e.g. an agonist), or indirectly, such as by increasing the expression or activity of a secondary molecule or compound (e.g. by increasing expression of BMP itself, or by increasing expression or activity of a downstream component of BMPR-mediated signalling) in the tumor stem cell or tumor progenitor cell which in turn increases BMPR-mediated signalling on a tumor stem cell or tumor progenitor cell.

Reference herein to "LIFR" includes reference to all forms of LIFR such as LIFR homologs, paralogs, orthologs, derivatives, fragments and functional equivalents. Reference herein to "BMPR" includes reference to all forms of BMPR such as BMPR homologs, paralogs, orthologs, derivatives, fragments and functional equivalents.

In the context of the present disclosure, an increase in LIFR or BMPR-mediated signalling refers to an increase of one to about 1000% of the normal level of LIFR or BMPR-mediated signalling. Alternatively, the LIFR or BMPR signalling activator can return the level of LIFR or BMPR-mediated signalling to normal in cases where signalling is less than normal.

Preferably, the increase in LIFR or BMPR-mediated signalling results in the modulation of any one or more of tumor stem cell and tumor progenitor cell properties such as, but not limited to, survival, self-renewal, proliferation, symmetric division and/or differentiation properties. Most preferably, the increase in LIFR or BMPR-mediated signalling alters the division properties of tumor stem cells and tumor progenitor cells and in particular a reduction in the probability of symmetric division or reduction in cell cycle frequency exhibited by proliferating tumor stem cells and tumor progenitor cells thereby leading to a reduction in the numbers of tumor stem cells and tumor progenitor cells.

The LIFR and BMPR signalling activators of the disclosure may be any proteinaceous molecules such as peptides, polypeptides and proteins, or they may be non-proteinaceous molecules. Methods for the isolation of LIFR and BMPR signalling activators are provided herein.

In relation to the present disclosure, mimetics are a particularly useful group of LIFR and BMPR signalling activators. The term is intended to refer to a substance which has some chemical similarity to the molecule it mimics, such as, for example, LIF, but which agonizes (mimics) its interaction with a target, such as, for example, a LIFR. A peptide mimetic is one class of mimetics, and may be a peptide-containing molecule that mimics elements of protein secondary structure (Johnson et al., Peptide Turn Mimetics in Biotechnology and Pharmacy, Pezzuto et al., Eds., Chapman and Hall, New York, 1993). The underlying rationale behind the use of peptide mimetics is that the peptide backbone of proteins exists chiefly to orient amino acid side chains in such a way as to facilitate molecular interactions such as those of antibody and antigen, enzyme and substrate or scaffolding proteins. A peptide mimetic, therefore, is designed to permit molecular interactions similar to the natural molecule.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large numbers of molecules for a target property. A mimetic of BMP-4, including a peptide mimetic for example, is specifically contemplated herein.

The goal of rational drug design is to produce structural analogs of biologically active polypeptides of interest or of small molecules with which they interact in order to fashion drugs which are, for example, more active or stable forms of the polypeptide, or which, for example, enhance or interfere with the function of a polypeptide in vivo (see, e.g. Hodgson, Bio/Technology 9:19-21, 1991). In one approach, one first determines the three-dimensional structure of a protein of interest by x-ray crystallography, by computer modelling or most typically, by a combination of approaches. Useful information regarding the structure of a polypeptide may also be gained by modelling based on the structure of homologous proteins. An example of rational drug design is the development of HIV protease inhibitors (Erickson et al., Science 249:527-533, 1990).

The capability of the LIFR and BMPR signalling activators of the present disclosure, whether they be proteinaceous or non-proteinaceous, to interact with LIFR or BMPR and/or increase LIFR or BMPR-mediated signalling (either directly or indirectly) in a stem or progenitor cell may be assessed via a number of screening methods which would be well known to a person skilled in the art. These may include screening naturally produced libraries, chemical produced libraries, as well as combinatorial libraries, phage display libraries and in vitro translation-based libraries.

Antibodies raised against LIFR and BMPR may be particularly useful as agonists that mimic the active configuration of LIF and BMP respectively. Suitable antibodies include polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies, and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24: 316-325 (1983)). Methods for producing antibody agonists are described in, for example, PCT publication WO 96/40281; U.S. Pat. No. 5,811,097; Deng et al., Blood 92 (6): 1981-1988 (1998); Chen et al., Cancer Res. 58 (16): 3668-3678 (1998); Harrop et al., J. Immunol. 161 (4): 1786-1794 (1998); Zhu et al., Cancer Res. 58 (15): 3209-3214 (1998); Yoon et al., J. Immunol. 160 (7): 3170-3179 (1998); Prat et al., J. Cell. Sci. 111 (Pt2): 237-247 (1998); Pitard et al., J. Immunol. Methods 205 (2): 177-190 (1997); Liautard et al., Cytokine 9 (4): 233-241 (1997); Carlson et al., J. Biol. Chem. 272 (17): 11295-11301 (1997); Taryman et al., Neuron 14 (4): 755-762 (1995); Muller et al., Structure 6 (9): 1153-1167 (1998); Bartunek et al., Cytokine 8 (1): 14-20 (1996); Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (which are all incorporated by reference herein in their entireties).

Nucleic acid ligands (also known as "aptamers") may also be particularly useful as agonists that mimic the active configuration of LIF and BMP respectively. For example, aptamers can be selected using the SELEX (Systematic Evolution of Ligands by Exponential Enrichment) method (Tuerk and Gold, 1990, Science 249: 505-510, which is incorporated by reference herein in its entirety). In the SELEX method, a large library of nucleic acid molecules (e.g., $10^{15}$ different molecules) is produced and/or screened with the target molecule, in this case BMPR, LIFR, or portions thereof. The target molecule is allowed to incubate with the library of nucleotide sequences for a period of time. Several methods can then be used to physically isolate the aptamer target molecules from the unbound molecules in the mixture and the unbound molecules can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure (i.e., aptamers truncated to their core binding domain). See, e.g., Jayasena, 1999, Clin. Chem. 45: 1628-1650 for review of aptamer technology, the entire teachings of which are incorporated herein by reference.

Essentially any chemical compound can be employed as a candidate LIFR or BMPR signalling activator. High throughput screening methodologies are particularly envisioned for the detection of such candidate activators. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37: 487-493; and Houghton et al., 1991, Nature, 354: 84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90: 6909-6913), vinylogous polypeptides (Hagihara et al., 1992, J. Amer. Chem. Soc., 114: 6568), nonpeptidal peptidomimetics with glucose scaffolding (Hirschmann et al., 1992, J. Amer. Chem. Soc., 114: 9217-9218), analogous organic synthesis of small compound libraries (Chen et al., 1994, J. Amer. Chem. Soc., 116: 2661), oligocarbamates (Cho et al., 1993, Science, 261: 1303), and/or peptidyl phosphonates (Campbell et al., 1994, J. Org. Chem., 59: 658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14 (3): 309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

Candidate LIFR and BMPR signalling activators may first be screened for their ability to bind to LIFR or BMPR, or to downstream components of the LIFR or BMPR signalling pathway, using a binding assay, and those candidates that bind may then be screened in a functional assay. Suitable binding assays include the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20 (8)).

An example of a method for functionally screening candidate LIFR and BMPR signalling activators includes the following steps:
  (i) Isolating a sample of tumor stem cells and/or tumor progenitor cells;
  (ii) placing aliquots of the tumor stem cells and/or tumor progenitor cells into suitable receptacles; and
  (iii) exposing the aliquots of tumor stem cells and/or tumor progenitor cells to candidate agents for a particular period of time and under particular conditions; and
  (iv) screening for morphological, physiological and genetic changes to the tumor stem cells and/or tumor progenitor cells.

Morphological, physiological and genetic changes includes screening for states of survival, self-renewal, proliferation and/or differentiation. An example of an assay that can be used is the Neural Colony Forming Cell Assay (NCFCA) described in United States Patent Application Publication No. 2005/0112546, incorporated herein by reference in its entirety. The NCFCA is able to distinguish stem cells from progenitor cells, both which have a proliferative potential and are capable of forming spheres in suspension culture (Neurosphere Assay) or colonies in the NCFCA. Briefly, primary or cultured cells obtained from a tumor are plated in a serum-free 3-D collagen matrix containing the mitogens FGF2 and EGF. Under these culture conditions only stem cells and progenitor cells with a proliferative potential divide forming well-defined colonies whose size can be measured after 1-4 weeks. Differences in colony size positively correlate to the proliferative potential of the founding cell and provide a readout of stem and progenitor cell frequency. Under these conditions only colonies greater than 2 mm in diameter are derived from a stem cell while those less than 2 mm in diameter are derived from progenitor cells. A meaningful and accurate readout of stem cell and progenitor cells allows one to screen for genetic and epigenetic elements that alter the frequency of these two cell types.

Another example of an assay for survival, self-renewal, proliferation and/or differentiation which may be used to screen for LIFR and BMPR receptors is performed as follows. First, cells from a disaggregated glioblastoma multiforme tumor are plated in serum free medium containing the mitogens FGF2 (fibroblast growth factor 2) and EGF (epidermal growth factor) as described by Gritti et al., J. Neurosci. (1996) 16(3):109-1100, incorporated herein by reference. This culture system selects away differentiating/differentiated cells from primary tumor cultures, leaving only the tumor stem cells free to proliferate and expand exponentially, thereby forming primary neurospheres. The primary neurospheres may dissociated and plated again in serum free medium at clonal density in the presence of EGF and FGF2 in microtitre plates. Candidate LIFR and BMPR signalling activators are added to each well of the microtitre plate, and the plates are incubated for a period of time sufficient to allow untreated cells to proliferate. At the end of incubation, the neurospheres are again dissociated and the process can be repeated for a predetermined number of additional passages in the presence of the candidate LIFR and BMPR signalling activators. At the end of the predetermined number of passages, the wells of the microtitre plate may be examined using a microscope for the presence of neurospheres, and the number and size of the neurospheres are determined, providing a measure of the effect of the candidate LIFR or BMPR signalling activator on stem and progenitor cells. The mathematical algorithms of Example 1 may be used to determine the number of stem cells and progenitor cells at the end of each passage. Comparison with untreated cells that were also serially passaged allows for the identification of candidate LIFR and BMPR signalling activators e.g. agents that attenuate the proliferation properties of stem and progenitor cells. The candidate LIFR and BMPR signalling activators may then be assayed on differentiated or differentiating cells to determine if the effect of the candidate agents is specific for tumor stem cells, rather than being generally cytotoxic.

LIFR and BMPR signalling activators may also include RNA interference (RNAi) molecules, ribozymes, or antisense oligonucleotides. Such molecules may reduce the expression of inhibitors of LIFR and BMPR signalling, and thus have the effect of activating LIFR and BMPR signalling.

The LIFR and BMPR signalling activators of the disclosure are useful for increasing LIFR or BMPR-mediated signalling in a tumor stem cell or tumor progenitor cell. Accordingly, the present disclosure provides a method of increasing LIFR or BMPR-mediated signalling in a tumor stem cell or tumor progenitor cell, the method comprising contacting the tumor stem cell or tumor progenitor cell with a LIFR and/or BMPR signalling activator for a time and under conditions sufficient to increase LIFR or BMPR-mediated signalling in the tumor stem cell or tumor progenitor cell. The LIFR and/or BMPR signalling activators may also used in combination with a LIF preparation and/or a BMP preparation as disclosed herein.

The disclosure also provides methods for the treatment or prevention of a disease or disorder characterized by excessive or misregulated cellular proliferation. The methods involve administering a therapeutically effective amount of LIFR and/or BMPR signalling activator to a subject or tissue thought to be undergoing such excessive or misregulated cellular proliferation. Preferably, the disorder characterized by excessive cellular proliferation is a brain disorder, more preferably a brain tumor including, but not limited to, acoustic neuroma, adenoma, astrocytoma, juvenile pilocytic astrocytoma, brain stem glioma, chordoma, choroid plexus, craniopharyngioma, ependymoma, ganglioglioma, ganglioglioneurocytoma, glioblastoma multiforme (GBM), glioma, lymphoma, medulloblastoma, meningioma, oligodendroglioma, optic nerve glioma, a pituitary tumor, a pineal tumor, or pineoblastoma. The LIFR and/or BMPR signalling activators may also administered in combination (either at the same time or at different times) with a LIF preparation and/or a BMP preparation as disclosed herein.

In another aspect the disclosure provides a method for reducing the growth of a tumor comprising administering a therapeutically effective amount of a LIFR signalling activator and/or a BMPR signalling activator to said tumor.

In a further aspect, the disclosure provides a method of decreasing the number of tumor stem cells and/or tumor progenitor cells in a tumor comprising contacting the tumor with a LIFR signalling activator and/or a BMPR signalling activator. Without being limited by theory or hypothesis, it is believed that when administered to a tumor, LIFR signalling activators and BMPR signalling activators lead to an increase in LIF or BMP-mediated signalling, which results in the modulation of any one or more of the following tumor stem cell or tumor progenitor cell properties such as, but not limited to, cell survival, self-renewal, symmetric division, proliferation and/or differentiation properties. In particular, it is believed that the increase in LIFR or BMPR-mediated signalling results in a reduction in the proliferation properties of stem and progenitor cells and in particular a reduction in the probability of symmetric division exhibited by proliferating stem cells or progenitor cell thereby reducing their numbers. Accordingly, in another aspect the disclosure provides methods for reducing the likelihood that a tumor stem cell or tumor progenitor cell undergoes a symmetrical division, the method comprising contacting the tumor stem cell or tumor progenitor cell with a BMPR signalling activator and/or a LIFR signalling activator.

In some embodiments of the present disclosure the LIFR and/or BMPR signalling activator may be administered to a subject directly such that endogenous tumor stem cells and tumor progenitor cells are regulated in vivo. In alternative embodiments of the present disclosure, tumor stem cells and tumor progenitor cells may be contacted with the agents of the present disclosure in vitro.

Methods for administering the LIFR signalling activators and/or BMPR signalling activators to a subject, including to a tumor, along with pharmaceutical compositions comprising LIFR signalling activators and/or BMPR signalling activators, are provided below in the section entitled "Administration and Pharmaceutical Compositions"

Administration and Pharmaceutical Compositions

As disclosed above, therapeutically-effective amounts of a LIF preparation and/or a BMP preparation and/or LIFR signalling activator and/or BMPR signalling activator may be, inter alia, administered to a subject or tissue to treat or prevent a disease or disorder characterized by excessive or misregulated cellular proliferation. For example, in one embodiment a therapeutically effective amount of a BMP-4 preparation or a BMP-4 mimetic is administered to a human patient suffering from GBM. In addition to the tumors and cancers described supra, other cancers that may be treated or prevented according to the methods disclosed herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, melanoma, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD).

In one embodiment, a LIF preparation and/or a BMP preparation and/or LIFR signalling activator and/or BMPR signalling activator is administered to a subject in the form of a pharmaceutical composition. Accordingly, in another aspect the present disclosure also provides pharmaceutical compositions which are useful for the treatment or prevention of a disease or disorder characterized by excessive or misregulated cellular proliferation. The pharmaceutical compositions of the disclosure comprise at least one agent selected from the group consisting of a LIF preparation, a BMP preparation, a LIFR signalling activator, and a BMPR signalling activator. For example, in one embodiment a pharmaceutical composition comprising a therapeutically effective amount of a BMP-4 preparation is provided for the treatment of GBM. In another embodiment, a pharmaceutical composition comprising a therapeutically effective amount of a BMP-2 preparation is provided for the treatment of GBM. In another embodiment, a pharmaceutical composition comprising a therapeutically effective amount of a BMP-5 preparation is provided for the treatment of GBM. In another embodiment, a pharmaceutical composition comprising a therapeutically effective amount of a BMP-6 preparation is provided for the treatment of GBM. In another embodiment, a pharmaceutical composition comprising a therapeutically effective amount of a BMP-7 preparation is provided for the treatment of GBM. In another embodiment, a pharmaceutical composition comprising a therapeutically effective amount of a BMP-8b preparation is provided for the treatment of GBM.

In another aspect, the disclosure discloses the use of a LIF preparation and/or a BMP preparation and/or LIFR signalling activator and/or BMPR signalling activator in the manufacture of a medicament for the treatment or prevention of a disease or disorder characterized by excessive or misregulated cellular proliferation. For example, the use of a BMP-4 preparation or a BMP-4 mimetic in the manufacture of a medicament for the treatment of glioblastoma multiforme is specifically contemplated.

The pharmaceutical compositions of the disclosure may comprise a single agent or they may comprise any combination of the aforementioned agents, for example a combination of LIF and BMP-4. Moreover, the pharmaceutical compositions may comprise more than one agent of a particular class, for example, two different LIF preparations, or two different BMPR signalling activators, for example BMP-2 and BMP-4.

The pharmaceutical compositions preferably comprise at least one pharmaceutically acceptable carrier. In such pharmaceutical compositions, a LIF preparation and/or a BMP preparation and/or a LIFR signalling activator and/or a BMPR signalling activator forms the "active compound." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Note that in embodiments where a tissue or cell thought to be undergoing excessive or misregulated cell proliferation is treated with a LIF preparation and/or a BMP preparation and/or LIFR signalling activator and/or BMPR signalling activator in vitro, a LIF preparation and/or a BMP preparation and/or LIFR signalling activator and/or BMPR signalling activator may or may not be in the form of a pharmaceutical composition.

Subject as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer) and any other organisms who can benefit from the agents of the present disclosure. There is no limitation on the type of animal that could benefit from the presently described agents. The most preferred subject of the present disclosure is a human. A subject regardless of whether it is a human or non-human organism may be referred to as a patient, individual, animal, host or recipient.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In embodiments of the disclosure where a proliferative disorder of the brain is treated, for example GBM, it is preferable that the pharmaceutical composition and/or method of administration are tailored to overcome the blood-brain barrier (BBB) and/or the blood-tumor barrier (BTB). Methods for delivering pharmaceutical compostions across the BBB are known in the art. For example, see Misra et al, (2003) J Pharm Pharm Sci 6:252-273, incorporated herein by reference in its entirety. Suitable methods include, but are not limited to, trans-cranial brain drug delivery methods such as intracerebral implantation, intracerebroventricular (ICV) infusion, and or convection enhanced diffusion (CED). Intracerebral implantation may be carried out using, for example, polymer beads (such as heparin acrylic beads) or polymer wafers (such as polifeprosan 20) impregnated with a LIF preparation and/or a BMP preparation and/or LIFR signalling activators and/or BMPR signalling activators). For example, intracerebral implantation may be carried out by stereotactically injecting BMP-4 loaded heparin acrylic beads into the tumor or into the resection cavity.

The pharmaceutical compositions of the disclosure, for example pharmaceutical compositions comprising BMP-2, BMP-4, BMP-5, BMP-6, BMP-7, or BMP-8b preparations (or combinations thereof), may be administered to an unresected tumor using these methods; alternatively, the pharmaceutical compositions may be administered to the resection cavity following tumor resection. In some embodiments, the pharmaceutical compositions are administered first intratumorally, and are then administered postoperatively following tumor resection.

In some embodiments, a LIF preparation and/or a BMP preparation and/or LIFR signalling activator and/or BMPR signalling activator is associated with a molecule that can bind to an exofacial epitope on a component of the blood-brain barrier (BBB) receptor-mediated transport (RMT) system. In this way, LIF preparation and/or a BMP preparation and/or a LIFR signalling activator and/or a BMPR signalling activator, can be transported across the BBB using the endogenous RMT system. For example, a LIF or BMP preparation may be conjugated to a monoclonal antibody (such as OX26) to the transferrin receptor (TfR) to enable trans-membrane transport of the conjugate. See, for example, Pardridge, Neurorx 2(1):3-14 (2005), incorporated herein by reference in its entirety. Nanoparticles may also be induced to cross the BBB by conjugation to, for example, OX26; such nanoparticles may also be conjugated to a LIF preparation and/or a BMP preparation and/or LIFR signalling activator and/or BMPR signalling activator. See for example, Olivier et al., Pharm Res. (2002) 19(8):1137-43, incorporated herein by reference in its entirety. In addition, liposomes conjugated to, for example, OX26 may be used to deliver encapsulated LIF preparation and/or a BMP preparation and/or LIFR signalling activator and/or BMPR signalling activator across the BBB. See Huwyler et al., Proc Natl Mad Sci USA. (1996) 93(24):14164-9, incorporated herein by reference in its entirety. In addition, agents and treatments that disrupt the BBB and the BTB may also be used to pass a LIF preparation and/or a BMP preparation and/or a LIFR signalling activator or a BMPR signalling activator through the BBB or BTB. For example, intracarotid infusion of the vasoactive agent bradykinin can selectively increase permeability in brain tumor capillaries. See Matsukado et al., Brain Res. (1998) 792(1):10-5, incorporated herein by reference in its entirety.

In one embodiment, nucleic acid molecules encoding for the LIF and BMP preparations, or for polypeptide and peptide LIFR or BMPR signalling activators, or for ribozymes, RNAi molecules, and antisense molecules that are LIFR or BMP signalling activators, are inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91: 3054-3057; Voges et al. (2003), Ann. Neurol. 54:479-487, each of which is incorporated herein by reference in its entirety). The pharmaceutical preparation of the gene therapy vector can include the gene therapy vector in an acceptable diluent or encapsulant (such as a liposome which contains the vector), or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. In one embodiment, nucleic acid molecules encoding LIF and BMP preparations, or for polypeptide and peptide LIFR or BMPR signalling activators, are transferred into mammalian neural cancer stem cells by lentiviral vectors, as described in Consiglio et al, Proc Natl Acad Sci USA. 2004 Oct. 12; 101(41):14835-14840, incorporated herein by reference in its entirety.

In some embodiments, a single active compound according to the disclosure is administered e.g. a single LIF preparation or a single BMP preparation. In other embodiments, multiple active compounds are co-administered e.g. two different LIF preparations; or a LIF preparation and a BMP preparation; or a BMPR signalling activator and two different BMP preparations. In addition, the active compounds of the disclosure may be co-administered with other pharmaceuticals, such as chemotherapeutic agents, radiation sensitizers, radiotherapeutics, and the like. Reference herein to "co-administered" means simultaneous administration in the same formulation or in two different formulations via the same or different routes or sequential administration by the same or different routes. Reference herein to "sequential" administration is meant a time difference of from seconds, minutes, hours or days between the administration of the two types of agents and/or pharmaceutical compositions. Co-administration of the agents and/or pharmaceutical compositions may occur in any order.

The treatment methods and pharmaceutical compositions disclosed herein may be used in conjunction with other treatments, including chemotherapy (such as carmustine, cisplatin, paclitaxol, temozolomide, PCV (procarbazine, lomustine, and vincristine) and IL13-PE38QQR) treatment with radiotherapeutics (such as radiolabelled antibodies or radiolabelled nucleic acid ligands), radiotherapy, and surgery (including tumor resection/surgical de-bulking). For example, BMP-4 preparations may be co-administered with chemotherapeutic agents following tumor resection surgery and radiation therapy for the treatment of GBM. These additional treatments may be used before and/or during and/or after treatment according to the methods disclosed herein.

EXAMPLES

The present disclosure is further described by the following non-limiting examples. Note that for Examples 19-23, the protocols used to obtain the recited results are provided in Examples 24-29.

Example 1

Serial Passage of Fetal Human Neural Stem Cells and Analysis of Stem and Progenitor Cell Frequency Based on Mathematical Modelling An algorithm was derived to calculate the number of neural stem cells and the number of neural progenitor cells present in serially passaged neurosphere cultures. For the purposes of this algorithm, all cells are divided into three categories:

1. Stem cells are defined as: undifferentiated cells capable of, (a) proliferation, (b) self renewal over an extended period of time, (c) able to generate a large number of progeny, and (d) the ability to give rise to all the cell types of the tissue from which it is obtained,
2. Progenitor cells are defined as: undifferentiated cells capable of, (a) proliferation, (b) limited self renewal ability, (c) generation of a limited number of progeny and (d) the ability to give rise to at least one type of progeny; and
3. Differentiated cells are defined as a cell with limited or no proliferation ability and expression of both lineage specific markers and mature functional properties.

The terms "stem cell" and NSC may be used interchangeably herein. Similarly, the terms "progenitor cell" and NPC may also be used interchangeably herein.

In describing this algorithm, a number of assumptions have been made:

1. A neurosphere is composed of stem cells, progenitor cells and differentiated cells.
2. Every neurosphere is grown from either a single stem cell or single progenitor cell.
3. A stem cell has an infinite lifetime and a progenitor cell has a finite lifetime. The finite lifetime is defined to be/passages.
4. A stem cell always forms a neurosphere and a progenitor cell will form a neurosphere unless it has reached the end of its lifetime.
5. Every neurosphere has a total of c cells which are of one of two possible compositions. The possible compositions are:
    a. in each neurosphere derived from a single stem cell the composition is s stem cells, p progenitor cells and the remainder are differentiated cells; and
    b. in each neurosphere derived from a single progenitor cell the composition is p progenitor cells with the remainder being differentiated cells.

An algorithm that describes the total number of cells, $T_n$, at each passage, n, has been derived. At the beginning of the experiment a stem cell derived neurosphere is dissociated, i.e., there are s stem cells, p progenitor cells and c–s–p differentiated cells. The stem and progenitor cells are allowed to grow into neurospheres of which the total number is s+p and the differentiated cells die. The total number of cells at the time of the first $T_1$ passage, is then given by the product of the total number of neurospheres with the number of cells in each neurosphere:

$$T_1 = (s+p)c = sc + pc \quad (1)$$

The second equality of the above equation is interesting because sc represents the total number of cells in stem cell derived neurospheres and pc represents the total number of cells in progenitor cell derived neurospheres.

Assuming that progenitor cells live for two generations, these neurospheres are now dissociated. At the first passage there are s stem cell derived neurospheres, each of which must contain s stem cells, p progenitor cells and c–s–p differentiated cells. Also at the first passage are the p progenitor derived neurospheres each of which in turn contains p progenitor cells and c–p differentiated cells. These newly dissociated cells will now grow into their own neurospheres, except the differentiated cells which die. The total number of cells at the time of the second passage, $T_2$, is then given by:

$$T_1 = sc + pc \qquad (2)$$

$$T_2 = (s+p)sc + (p)ps = s^2c + spc + p^2c \qquad (3)$$

The first column on the right hand side of the equality contains the terms that represent the stem cell derived neurospheres. The second column represents the progenitor derived neurospheres.

The second equality in the $T_2$ equation represents the total number of cells in an expanded form. The $s^2c$ terms denotes the total number of cells in the stem cell derived neurosphere which will in the next generation become stem cell derived neurospheres. The second term, spc, represents the total number of cells in stem cell derived neurospheres which in the next generation become progenitor cell derived neurospheres. The last term, $p^2c$, represents the progenitor cell derived neurospheres which, depending on their lifetime, will either become progenitor cell derived neurospheres or die.

These cells are now passaged leading to the third generation. The total number of cells in this generation depends on the lifetime of the progenitor cells. If the lifetime is only two generations then the progenitor derived progenitor cells will now die rather than create a new neurosphere. Under this assumption, the total number of cells at the time of the third passage, $T_3$ is given by:

$$T_1 = sc + pc \qquad (4)$$

$$T_2 = s^2c + spc + p^2c \qquad (5)$$

$$T_3 = (s+p)s^2c + (p)psc + 0 = s^3c + s^2pc + p^2sc \qquad (6)$$

Similarly the total number of cells at the time of the fourth passage can be determined. Rewriting these equations yields:

$$T_1 = cs\left(1 + \frac{p}{s}\right) \qquad (7)$$

$$T_2 = cs^2\left(1 + \frac{p}{s} + \left(\frac{p}{s}\right)^2\right) \qquad (8)$$

$$T_3 = cs^3\left(1 + \frac{p}{s} + \left(\frac{p}{s}\right)^2\right) \qquad (9)$$

$$T_4 = cs^4\left(1 + \frac{p}{s} + \left(\frac{p}{s}\right)^2\right) \qquad (10)$$

Thus, by induction, we can say that at the $n^{th}$ passage the total number of cells will be given by $$T_n = cs^n\left(1 + \frac{p}{s} + \left(\frac{p}{s}\right)^2\right) \text{ where } n \geq 2. \qquad (11)$$

It should be repeated that this equation is based on the assumption that the progenitor lifetime is two generations.

If the lifetime of the progenitor cells is longer than two generations, the total number of cells at the time of the third passage, $T_3$ is given by $$T_1 = sc + pc \qquad (12)$$

$$T_2 = s^2c + spc + p^2c \qquad (13)$$

$$T_3 = (s+p)s^2c + (p)psc + (p)p^2c = s^3c + s^2pc + p^2sc + p^3c \qquad (14)$$

If the progenitor lifetime is three generations then the total number of cells by the fourth generation is given by:

$$T_1 = cs\left(1 + \frac{p}{s}\right) \qquad (15)$$

$$T_2 = cs^2\left(1 + \frac{p}{s} + \left(\frac{p}{s}\right)^2\right) \qquad (16)$$

$$T_3 = cs^3\left(1 + \frac{p}{s} + \left(\frac{p}{s}\right)^2 + \left(\frac{p}{s}\right)^3\right) \qquad (17)$$

$$T_4 = cs^4\left(1 + \frac{p}{s} + \left(\frac{p}{s}\right)^2 + \left(\frac{p}{s}\right)^3\right) \qquad (18)$$

Thus with this specific assumption, by induction, we can say that the total number of cells at the $n^{th}$ passage is given by $$T_n = cs^n\left(1 + \frac{p}{s} + \left(\frac{p}{s}\right)^2 + \left(\frac{p}{s}\right)^3\right) \text{ where } n \geq 3 \qquad (19)$$

In general, by a similar argument we can show that if the progenitor cell lifetime is l generations then the total number of cells at the $n^{th}$ passage is given by $$T_n = cs^n \sum_{i=0}^{n} \left(\frac{p}{s}\right)^i \text{ where } n < l \qquad (20)$$

$$T_n = cs^n \sum_{i=0}^{l} \left(\frac{p}{s}\right)^i \text{ where } n \geq l \qquad (21)$$

There is a well known simplification for the summation in the above equation, $$\sum_{i=0}^{l} r^i = \frac{1 - r^{l+1}}{1 - r} \qquad (22)$$

Thus the $T_n$ expression simplifies to:

$$T_n = cs^n \left[\frac{1 - \left(\frac{p}{s}\right)^{n+1}}{1 - \frac{p}{s}}\right] \text{ where } n < l \qquad (23)$$

$$T_n = cs^n \left[\frac{1 - \left(\frac{p}{s}\right)^{l+1}}{1 - \frac{p}{s}}\right] \text{ where } n \geq l. \qquad (24)$$

Since, for a given cell type, p, s, c and l are fixed, we can replace the term in square brackets by a constant, thus:

$$T_n = B_1 s^n \text{ where } n \geq l \quad (25)$$

and $$B_1 = c\left[\frac{1-\left(\frac{p}{s}\right)^{l+1}}{1-\frac{p}{s}}\right]. \quad (26)$$

This equation can be represented in a linear form by taking the logarithm of Equation (25) to get $$\log T_n = n \log s + \log B \text{ where } n \geq l. \quad (27)$$

Examining Equation (27), the slope of this straight line is log s and the y-intercept is log B. From an experimental point of view this means that if the log of the total number of cells is plotted against the passage number then the number of stem cells in a neurosphere can be calculated by examining the slope of the plot and the number of progenitor cells can be calculated by examining the y-intercept. When constructing this plot one must be careful to only include the data points which are at passage numbers greater than the lifetime of the progenitor cells. The lifetime of the progenitor cells is calculated by noting that for $l \geq n$, the ratio of the total number of cells at given passage to the passage is constant $$\left(\frac{T_{n+1}}{T_n} = s\right)$$

but that for l<n this ratio is not constant. Hence l=n+1, where n is the largest integer for which this ratio is not equal to s. This technique can be adapted to handle noisy data.

It is important to note that the first l−1 passages, (1, log $T_1$), ..., (l−1, log $T_{l-1}$), do not lie on the straight line. This can be seen by examining Equations (23) and (24).

From Equation (27) it can be seen that the number of progenitor cells in a neurosphere, p does not affect the slope of the line. If the slope changes, this must mean that the number of stem cells change. If the slope is 0, i.e., if the line is horizontal, then there is only one stem cell in a neurosphere and hence the total numbers of cells at each passage does not expand.

If the conditions under which the neurospheres grow are changed, for example if the growth factor is changed from only EGF to only EGF+FGF, then the slope of the line is still solely determined by the number of stem cells in a neurosphere. The proof of this assertion constitutes the remainder of this section.

Suppose that the conditions change after the $r^{th}$ passage and the number of stem cells that are produced changes to q, the number of progenitor cells to w, and the lifetime of the progenitor cells to m generations (for convenience we will assume that m≤l but the case where m>l is similar). The total number of cells after r+1 passages is given by:

$$T_{r+1} = (q+w)s^r c + w \sum_{i=0}^{m-1} \left(\frac{p}{s}\right)^i \text{ where } m \leq l \quad (28)$$

After r+m−1 passages the total number is:

$$T_{r+m-1} = cs^r q^{m-1} \sum_{i=0}^{m-1} \left(\frac{w}{q}\right)^i + w^{m-1}\left(\frac{p}{s}\right) \quad (29)$$

and after r+m passages the total number is:

$$T_{r+m} = cs^r q^m \sum_{i=0}^{m} \left(\frac{w}{q}\right)^i \quad (30)$$

By induction, the total number of cells after r+N passages is then:

$$T_{r+N} = q^N s^r c \sum_{i=0}^{m} \left(\frac{w}{q}\right)^i \quad (31)$$

$$= B_r q^N \quad (32)$$

where:

$$B_r = s^r c \sum_{i=0}^{m} \left(\frac{w}{q}\right)^i \quad (33)$$

Linearising, $$\log T_N = N \log q + \log B, \quad (34)$$

Thus, as before, it can see that after the change of conditions the slope of this line is only affected by the number of stem cells.

Based on the above algorithm stem cell and progenitor cell frequency can be calculated from the following steps:

1. serially passing cells in the neurosphere assay and plotting total number of cells generated at each passage based on multiplying the total cells of the previous passage by the fold increase in cells generated of the current passage;
2. linearising the logarithmic growth curve by taking the log of the total cells generated at each passage;
3. calculating the line of best fit and then using the formula for a straight line (y=mx+b) to calculate the slope of the line and the y-intercept, which in turn reveals the number of stem cells and the number of progenitor cells using the formulae above.

Example 2

Serial Passage of Fetal Human Neural Stem Cells and Analysis of Stem and Progenitor Cell Frequency Based on Mathematical Modeling The mathematical model of Example 1 was applied to serially passaged fetal human neural stem cells. Fetal human neural stem cells were serially passaged using conventional techniques (i.e. cells are plated at clonal density at each passage using a fraction of the cells from the previous passage, and using serum free medium supplemented with the mitogens EGF and FGF2), as described in Vescovi et al. (1999) Exp. Neurol. 156:71-83, incorporated herein by reference in its entirety. At the end of each passage, the total number of cells was determined by dissociating the cells into a single cell suspension and counting the cells single cell suspension and counting the number of viable and dead cells by trypan blue exclusion cells. The theoretical total number of cells at the end of each passage (which is a function of the total number of cells counted at the end of the passage and the fraction of the immediately prior passage that was replated to yield the counted cells) was plotted vs. passage number (FIG. 1A) to yield a growth curve. The log of the total number of cells at the end of each passage was also plotted vs. passage number (FIG. 1B). A best-fit trend line for the linear log plot was generated (FIG. 1B) and the formula for a straight line (y=mx+b) was used to determine the slope and the y-intercept. Stem cell and progenitor cell frequency were then calculated according to equations (26) and (27) in Example 1 (with n=1, l=n+1=2, c=1,000; these values are also used in all of the following examples). Stem cell frequency was calculated to be 0.24% of the total cell population, and progenitor cell frequency was calculated to be 1.15% of the total cell population.

Example 3

Analysis of Stem and Progenitor Cell Frequency of Fetal Human Neural Stem Cells in the Neural Colony Forming Cell Assay The Neural Colony Forming Cell Assay (NCFCA) may be used to determine stem and progenitor cell frequency based on an analysis of neural colony size. The NCFCA is described in United States Patent Application Publication Serial No. 2005/0112546, published May 26, 2005, incorporated herein by reference in its entirety. Briefly, the NCFCA is performed by suspending neural cells in a semi-solid medium, preferably a collagen-based or methylcellulose-based (IMDM, DMEM/F12, McKoy's, Iscoves) semi-solid medium. The semi-solid medium may comprise the same suitable medium used to culture the neural cells (e.g. Neurocult™ [StemCell Technologies, Inc.] serum free medium without cytokines plus Neurocult™ Proliferation Supplements plus EGF) to which collagen or methylcellulose is added. The medium is preferably serum free. Cells in the semi-solid medium are plated at a concentration that will allow sufficient number of colonies for statistical analyses of the data (e.g. 1,000-25,000 cells, preferably 2,500-7,500 per 35 mm culture dish). The colonies which are formed arise from a single cell—either a neural stem cell or progenitor cell. The colonies are cultured until size and differences can be discerned between colonies sizes (e.g. about 10-30 days), then colonies are counted and colony size is estimated using grids on a scoring dish. Colonies which were generated from a single neural stem cell will continue to grow in size over time, while colonies generated from a neural progenitor cell will have a limited ability to grow and hence not continue to grow in size over time. Colony size will distinguish between High Proliferative Potential-NSC (HPP-NSC), Low Proliferative Potential-NSC (LPP-NSC) and Neural Progenitors cells. Therefore, the size of the colony generated can be indicative of whether the colony was generated from a neural stem cell or neural progenitor cell and further whether the NSC have high or low proliferative potentials. In particular, the larger colonies (as compared to the other colonies on the dish) are indicative of high proliferative potential neural stem cells, mid-sized colonies are indicative of low proliferative potential neural progenitor cells, and the smaller colonies are indicative of neural progenitor cells. The actual diameter of the "larger colonies" or "smaller colonies" will depend on many factors, such as how long the colonies are cultured etc. For example, after culturing 2,500 cells/dish for 14-28 days, colonies were classified into one of four categories based on diameter: (1) >2.0 mm, (2) 1-2 mm, (3) 0.5-1 mm and (4) <0.5 mm. Therefore, assuming the colonies are cultured for at least 14 days, a diameter of greater than 2.0 mm is indicative of a colony generated from a neural stem cell. Cell types in the NCFCA can also be distinguished based on morphologies they produce. Undulated colonies are produced by neural stem cells, whereas colonies with a smooth periphery are produced by neural progenitor cells. Kits for performing the NCFCA are commercially available from StemCell Technologies, Inc.

Stem and progenitor cell frequency for fetal human neural stem cells was calculated by plating cells in the NCFCA. Passage 12 fetal neural stem cell progeny were dissociated into a single cell suspension and plated at a density of 2000 cells/ml together with 20 ng/ml of EGF and 10 ng/ml of bFGF. Cells were cultured in the semi-solid medium for 3 weeks after which the frequency and size of colonies were calculated. Less than 2% of the total cells plated formed colonies exhibiting stem cells characteristics. Thus, the results in Example 2 from the mathematical analysis method are consistent with the results of the NCFCA.

Example 4

Figure 2:
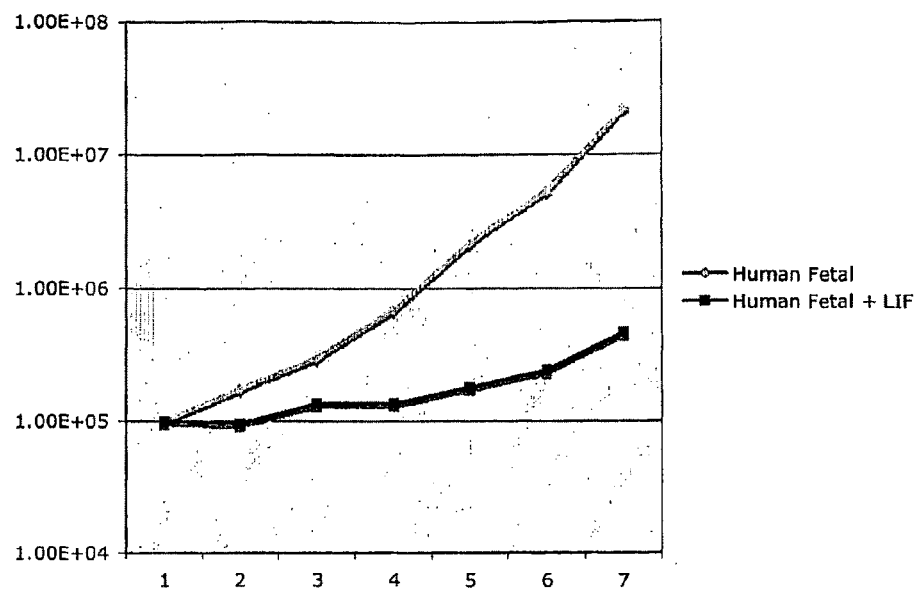
FIG. 2A shows a plot of the theoretical total number of cells at the end of each passage vs. passage number for human neural stem cells with and without the addition of LIF.
FIG. 2B shows the log of the total number of cells at the end of each passage vs. passage number and a best-fit trend line for the linear log plot.
FIG. 2C shows graphically the reduction in stem cell and progenitor cell frequency in the presence of LIF.
Figure 2:
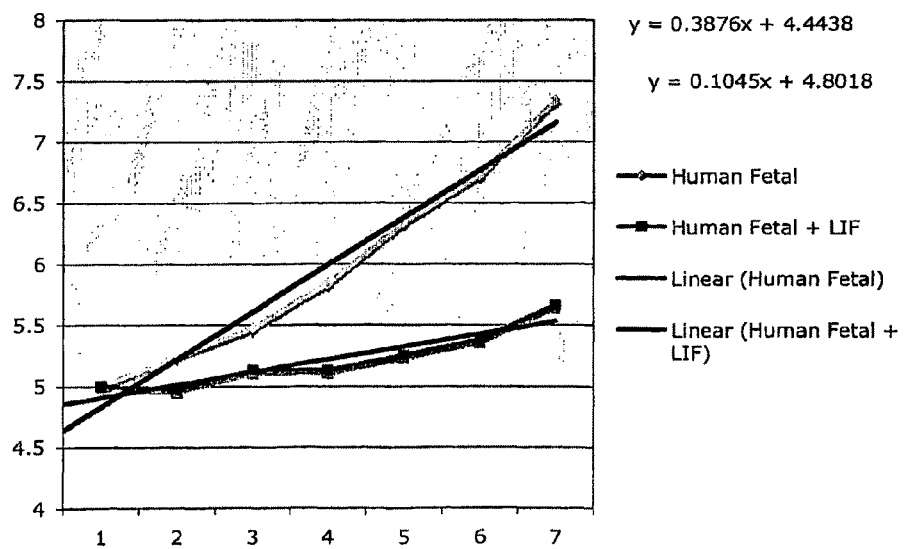
Figure 2:
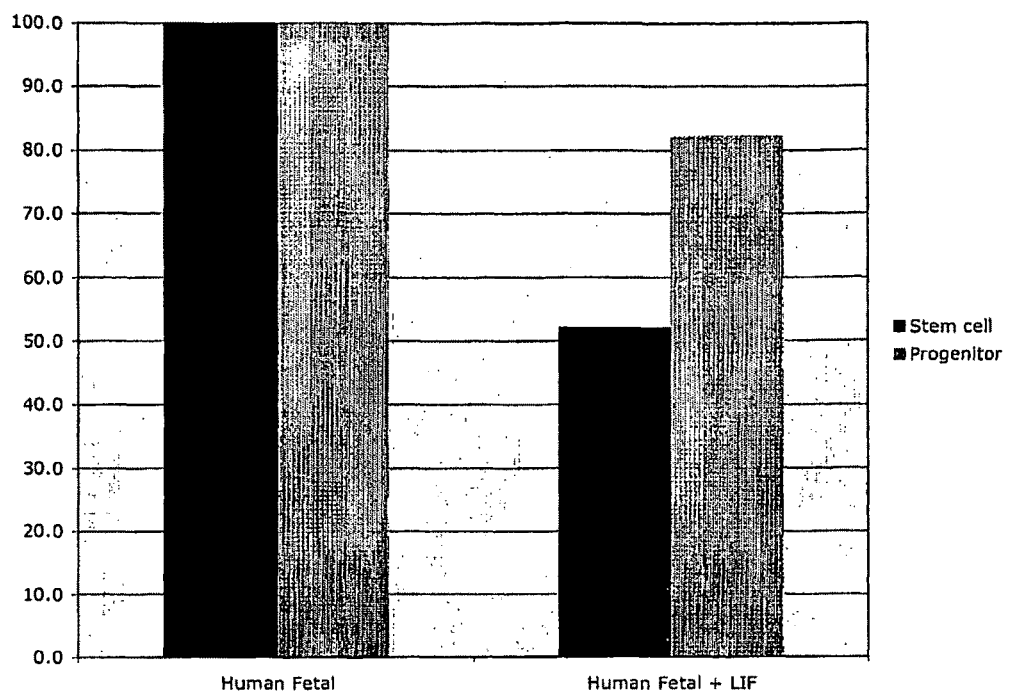

Leukemia Inhibitor Factor (LIF) Reduces Stem and Progenitor Cell Frequency in Serially Passed Fetal Human Neural Stem Cells Serially passed fetal human neural stem cells were cultured in normal proliferation conditions as in Example 2 (including the mitogens FGF2 and EGF) with or without the addition of 20 ng/ml of human LIF. Growth curves were generated for both groups (FIG. 2A), converted to a linear scale by taking the log of the theoretical total number of cells generated at the end of each passage (see Example 2) and the slope and y-intercept was determined based on best fit trendline (FIG. 2B). Analysis of stem and progenitor cell frequency according to the method of Example 1 revealed a 48% reduction in stem cell frequency and an 18% reduction in progenitor cell frequency in the presence of LIF (FIG. 2C; y-axis represents % of control value). Hence, LIF can be used to reduce neural stem cell and neural progenitor cell frequency in serially passed human neural stem cells.

Example 5

Bone Morphogen Protein 2 BMP-2) Reduces Stem Cell and Progenitor Cell Frequency in Serially Passed Fetal Human Neural Stem Cells Serially passed fetal human neural stem cells were cultured in normal proliferation conditions (including the mitogens FGF2 and EGF) as in Example 2 with or without the addition of 20 ng/ml of human BMP-2 protein. Growth curves were generated for both groups, converted to a linear scale by taking the log of the theoretical total number of cells generated at the end of each passage and determining the slope and y-intercept based on best fit trendline. Analysis of stem and progenitor cell frequency by the method of Example 1 revealed a reduction in both cell types in the presence of BMP-2. Hence, BMP can be used to reduce neural stem cell frequency and neural progenitor cell frequency in serially passed human neural stem cells.

Example 6

Figure 3:
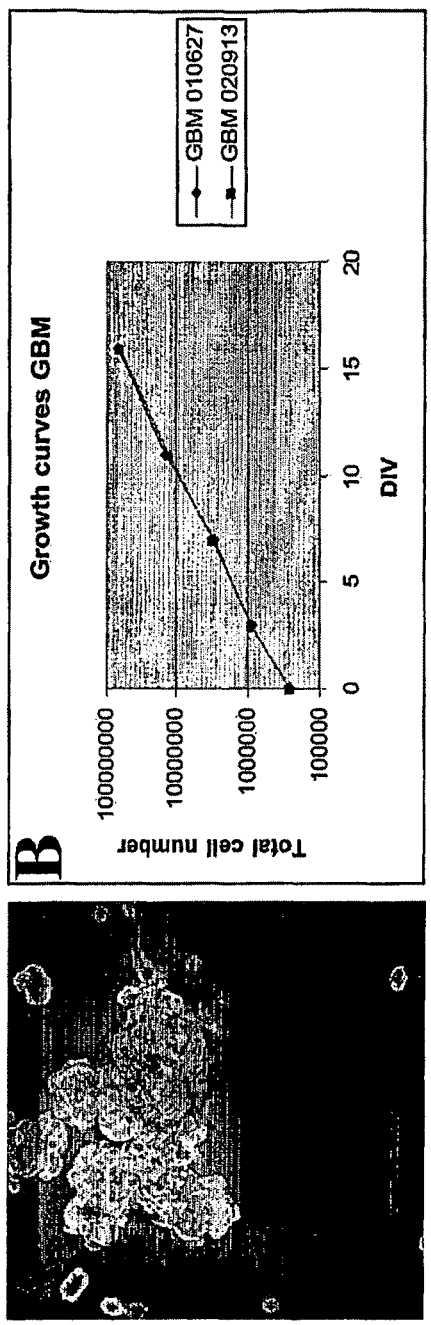
FIG. 3A depicts a phase contrast 20× view of a tumor cell neurosphere.
FIG. 3B depicts the theoretical total cell number at each division for two different GBM cell lines.

Serially Passaged Cells Derived from Glioblastoma Multiforme (GBM) Exhibit Key Stem Cell Features Human GBM contain tumor neural stem cells (tNSC) that proliferate under conditions tailored to allow ex vivo growth of neural stem cells. See Galli et al. (2004) Cancer Research 64:7011-7021, incorporated herein by reference in its entirety. The tNSCs may be isolated from tumor samples according to the method of Galli et al (2004), supra, and Vescovi et al., Exp. Neurol. 156:71-83 (1999), incorporated herein by reference in its entirety. Briefly, tNSCs may be isolated by first dissociating the tumor samples by trituration in Dulbecco's modified Eagle's medium (DMEM)/F12 containing 07. mg/mL ovomucoid. Cells are collected by centrifugation and resuspended in growth factor-free, chemically defined NS-A medium (Stem Cell Technologies, Vancouver, BC, Canada) containing 2 mM glutamine, 0.6% glucose, 9.6 gm/mL putrescine, 6.3 ng/mL progesterone, 5.2 ng/mL sodium selenite, 0.025 mg/mL insulin, 0.1 mg/mL transferrin. Viable cells are then plated in 25 cm$^2$ tissue culture flasks at density (2,500-5,000 cells/cm2) in the same chemically defined NS-A medium plus 20 ng/mL EGF and 20 ng/mL FGF2. The medium is replaced with fresh medium every 24-48 hours if necessary. Five to 20 days after plating, tumor cell neurospheres can be observed (see FIG. 3A, which depicts a phase contrast 20× view) that resemble the classical neurospheres formed in vitro by normal neural stem cells, as described by Reynolds & Weiss (1992) Science 255:1707-1710, incorporated herein by reference in its entirety. The tumor cell neurospheres may be dissociated and serially re-passaged under the same conditions, whereupon the tNSCs establish new tumor cell neurospheres. The tNSCs stably self-renew and expand in culture (see FIG. 3B which depicts the theoretical total cell number at each division for two different GBM cell lines). The tNSCs are multipotential in vitro since their progeny produce neurons, oligodendrocytes, and astrocytes under differentiating conditions. For example, staining of differentiated progeny with an anti-beta-tubulin antibody, an anti-glial fibrillary acidic protein (GFAP) antibody-(GFAP is a marker of astroglial differentiation), and with an anti-galactocerebroside (GalC) antibody was observed (GalC is a marker for oligodendrocytes).

When transplanted into the brains of immuno-deficient mice, the tNSCs generate GBM with immunoreactivity for astroglial-specific markers, just as in typical human GBM. When these tumors are themselves removed and tNSCs recultured, the secondary tNSCs regenerate GBM when transplanted in the brains of immuno-deficient mice. Thus, human tNSCs are unipotential in vivo, multipotential in vitro, can act as tumor-founding cells down to the clonal level, and can establish tumors in mice that closely resemble key features of the human disease even after serial retransplantation. Human tNSCs therefore seem to be involved in the growth and recurrence of human GBM.

Example 7

Figure 4:
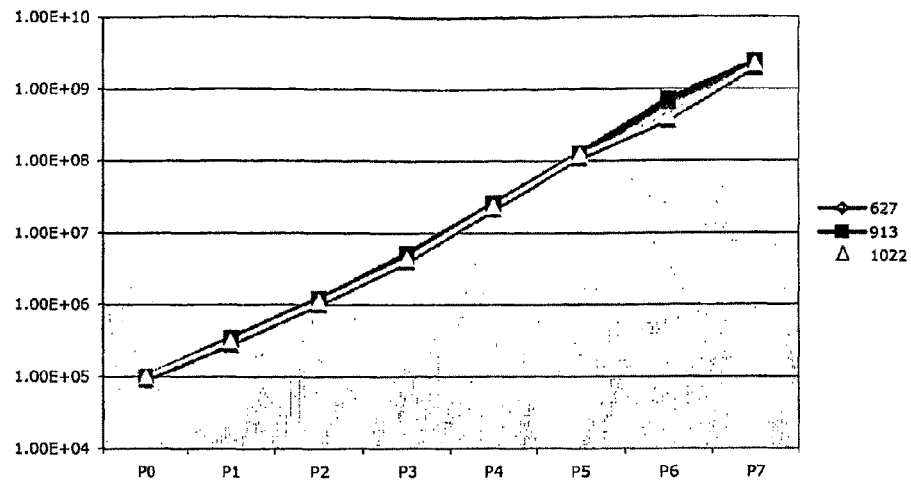
FIG. 4A shows a plot of the theoretical total number of cells at the end of each passage vs. passage number for serially passed GBM tumor cells.
FIG. 4B shows the log of the total number of cells at the end of each passage vs. passage number and a best-fit trend line for the linear log plot.
FIG. 4C shows graphically the tumor stem cell and tumor progenitor cell frequency.
Figure 4:
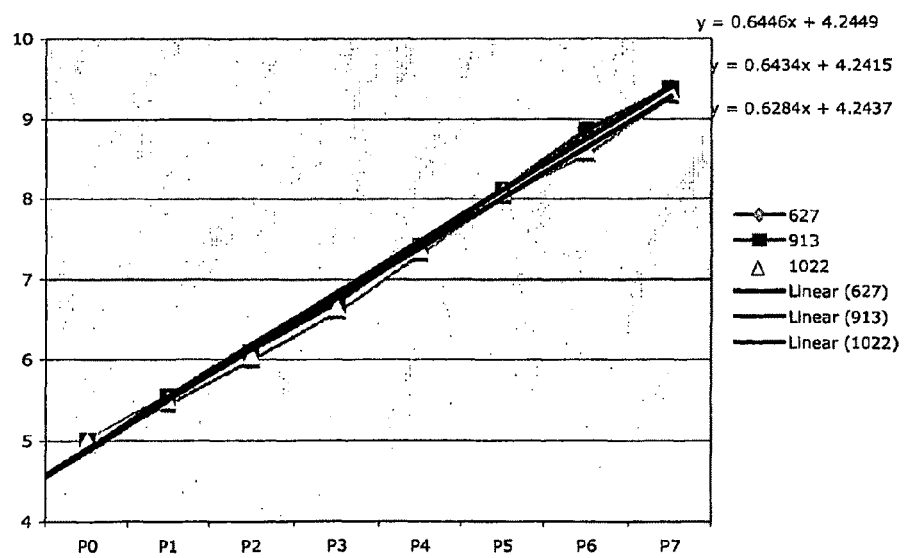
Figure 4:
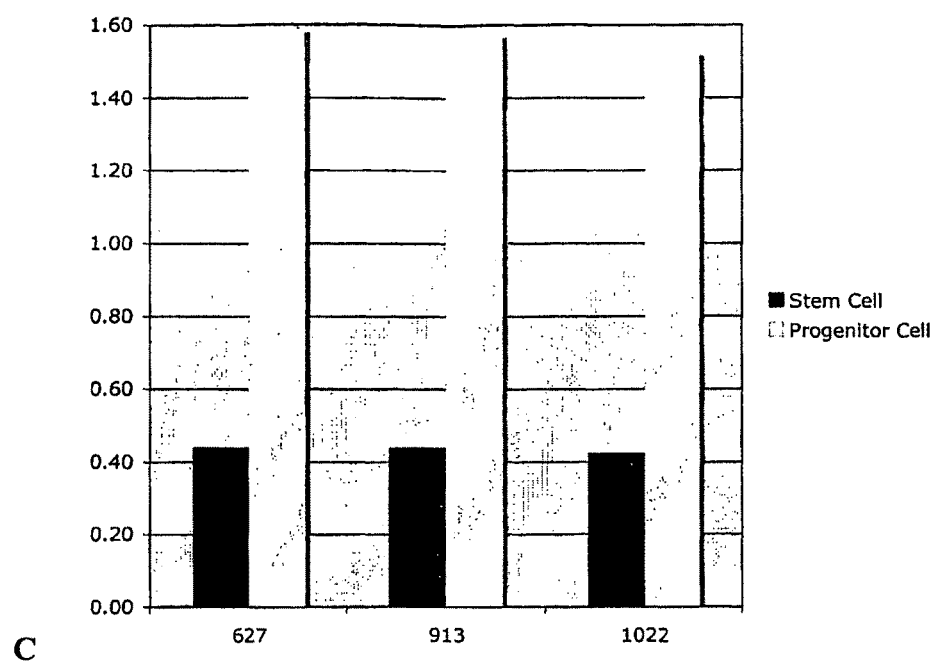

Use of Mathematical Modelling of Serially Passed GBM Tumor Cells to Calculate Tumor Stem Cell and Tumor Progenitor Cell Frequency Stem cell and progenitor cell frequency was determined for three GBM cell lines using the analysis method of Example 1. The cell lines were derived from the tumors of three different patients (tumors obtained from the Neurological Institute C. Besta and classified according to World Health Organization (WHO) guidelines). The tumor cells were serially passed using the methods of Example 6, and the theoretical total number of cells generated was plotted for each passage for each cell line (627, 913, 1022) (see FIG. 4A). The log of the theoretical total number of cells generated at the end of each passage was calculated and based on a best fit-treadline, the slope and y-intercept were calculated (see FIG. 4B). The frequency of the number of stem and progenitor cells was calculated using the method of Example 1. The tumor stem cell frequency was 0.44% of the total cells, and the tumor progenitor cell frequency was 1.56% of the total cells (depicted for each of the three GBM cell lines in FIG. 4C).

Example 8

Calculation of Tumor Stem Cell and Tumor Progenitor Cell Frequency from GBM Tumor Stem Cell Derived Progeny in the Neural Colony Forming Cell Assay (NCFCA)

Figure 5:
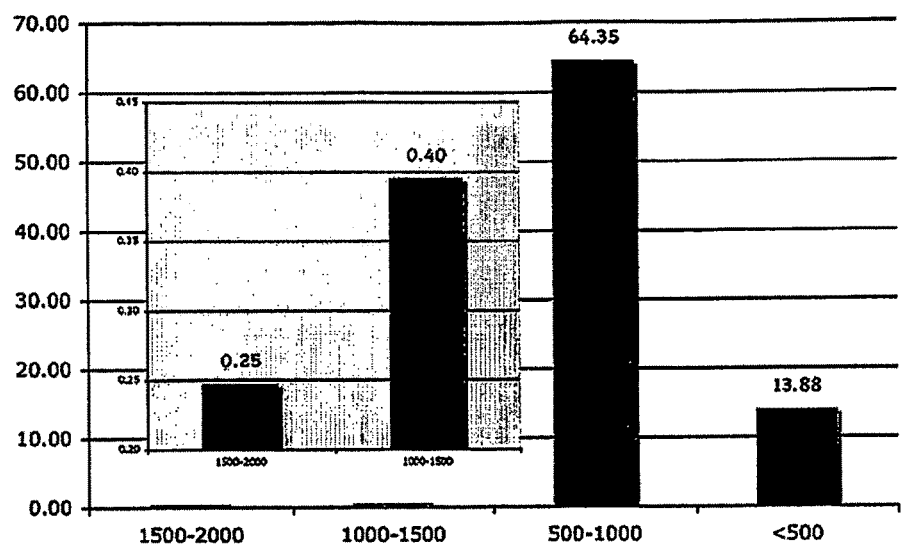
FIG. 5 main graph shows the % of total cells plated (y-axis) that form colonies in the following diameter size ranges in the Neural Colony Forming Cell Assay (NCFCA) for serially passed GBM tumor cells: 1,500-2,000 μm; 1,000-1,500 μm; 500-1,000 μm; and <500 μm). The inset to the main graph in FIG. 5 shows the % of total cells plated (y-axis) that form colonies in the 1,500-2,000 μm and 1,000-1,500 μm diameter categories, using a different y-axis scale than the main graph.

Passage 15 GBM cells were plated in the Neural Colony Forming Cell Assay (NCFCA) as described in Example 3. Cultures were fed weekly with fresh media and after 3 weeks colony diameter was determined. In this assay only the largest colonies exhibit stem cell characteristics following extraction from the semi-solid medium and sub-cloning. Between 0.25% to 0.65% of the total cells plated formed large colonies. See main graph in FIG. 5 which shows the % of total cells plated (y-axis) that form colonies in the following diameter size ranges: 1,500-2,000 µm; 1,000-1,500 µm; 500-1,000 µm; and <500 µm). The inset to the main graph in FIG. 5 shows the % of total cells plated (y-axis) that form colonies in the 1,500-2,000 µm and 1,000-1,500 µm diameter categories, using a different y-axis scale than the main graph. Thus, the NCFCA and the mathematical analysis of Example 7 yield a similar frequency for tumor stem cells in the GBM tumor cell lines.

Example 9

Presence of all of the Forms of BMP Receptors in Primary Tumor Samples and tNSCs Expression of the three BMP receptors (BMPR1a, BMPR1b and BMPR2) was determined by real time PCR in:
1. Primary human brain tumor specimens: anaplastic astrocytoma (AA 031217); glioblastoma (GBM050203, GBM 040114, GBM 040202, GBM 050207, GBM 050208); and disembryoblastic neuroepithelial neoplasia (NND 040115);
2. normal human fetal neural stem cells (fNSCs); and
3. human glioblastoma tumor neural stem cell (tNSC) lines (GBM010627, GBM 020913, GBM 021022) prepared according to the method of Example 6

The following method was used. First, total RNA was isolated from fNSCs, tNSCs and from the primary tumor samples using the TRIzol reagent (Life Technologies, Rockville, Md.), and then reverse-transcribed using SuperScript Rnase H-Reverse Transcriptase (Life Technologies, Rockville, Md.). All cDNAs used as templates were previously normalized using Glyceraldehyde-3-phosphate dehydrogenase (GAPDH) as a housekeeping gene and MCF-7 cell line as a positive control. Quantitative Real-Time PCR reactions were then run in triplicate using primers specific for each BMP receptor and using Brilliant® SYBR® Green QPCR Core Reagent Kit (STRATAGENE, La Jolla, Calif., USA). SYBR Green dye binds to any PCR product, and therefore does not require the use of sequence specific probes. The Brilliant SYBR Green master mixes contain dUTP for use with the UNG decontamination protocol. The primer sequences used are as follows:

Primer Sequences x Reverse Transcribed (RT) PCR

```
hBMPR-1A    Fw:  5'-AATGGAGTAACCTTAGCACCAGAG-3'
            SEQ ID NO: 1 hBMPR-1A    Rw:  5'-AGCTGAGTCCAGGAACCTGTAC-3'
            SEQ ID NO: 2 hBMPR-1B    Fw:  5'-GGTTGCCTGTGGTCACTTCTGG-3'
            SEQ ID NO: 3 hBMPR-1B    Rw:  5'-TAGTCTGTGATTAGGTACAACTGG-3'
            SEQ ID NO: 4 hBMPR-2     Fw:  5'-TCAGATATATGGCACCAGAAGTG-3'
            SEQ ID NO: 5 hBMPR-2     Rw:  5'-GTGGAGAGGCTGGTGACACTTG-3'
            SEQ ID NO: 6
```

Primer Sequences x Real Time PCR

```
hBMPR1a     Fw:  5'-caggttcctggactcagctc-3'
            SEQ ID NO: 7 hBMPR1a     Rw:  5'-ctttccttgggtgccataaa-3'
            SEQ ID NO: 8 hBMPR1b     Fw:  5'-aaaggtcgctatggggaagt-3'
            SEQ ID NO: 9 hBMPR1b     Rw:  5'-gcagcaatgaaacccaaaat-3'
            SEQ ID NO: 10 hBMPR2      Fw:  5'-gctaaaatttggcagcaagc-3'
            SEQ ID NO: 11 hBMPR2      Rw:  5'-cttgggccctatgtgtcact-3'
            SEQ ID NO: 12
```

Fluorescent emission was recorded in real-time (Chromo 4 Four-Color Real-Time PCR Detector, MJ Research, BIO-RAD, USA). Gene expression profiling was completed using the Comparative Ct method of relative quantification (Higuchi et al). For each gene, relative RNA quantities were normalized to two endogenous controls, GAPDH and 18s rRNA. Each replicate was normalized and the average relative quantity (RQ) is reported for each gene. The mean fold changes were calculated along with standard deviation and 95% confidence intervals of the three replicates.

Figure 6:
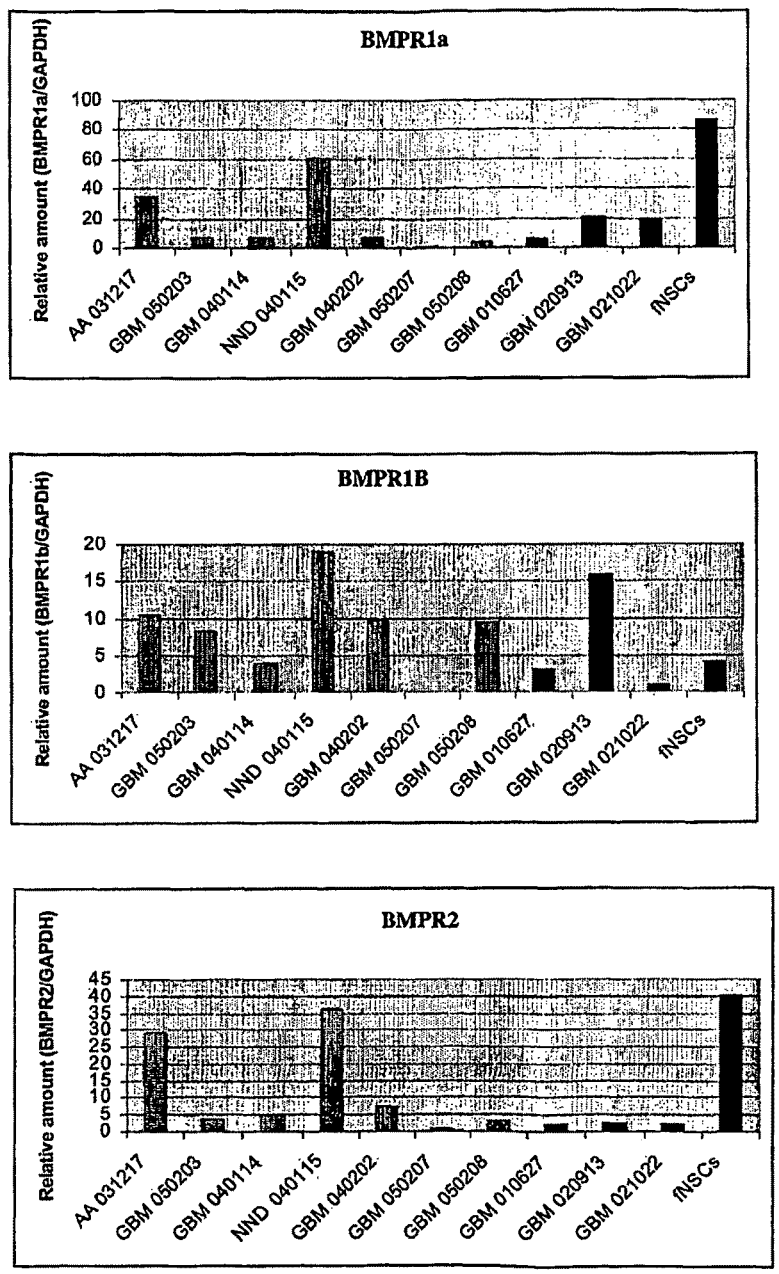
FIG. 6 shows real time PCR results in primary human tumor specimens and human tumor neural stem cell lines for BMPR1a, BMPR1b, and BMPR2.

FIG. 6 depicts the results. The results indicate that different tumors having different degrees of aggressiveness have characteristic BMPR expression profiles. Thus, the BMPR expression profile of a tumor may be used in a diagnostic method to characterize the tumor and to predict the aggressiveness of the tumor.

Example 10

Figure 7:
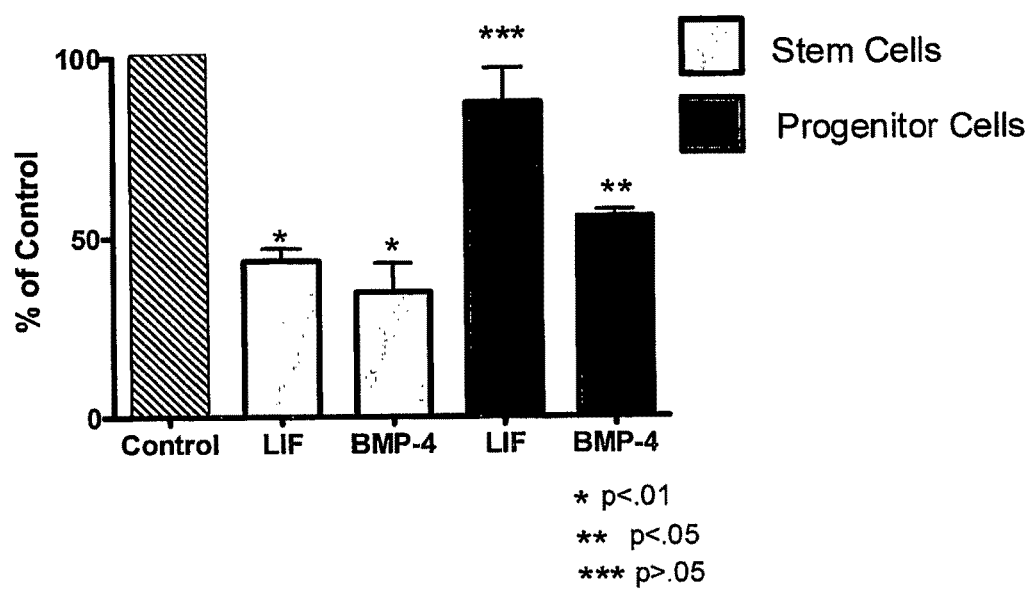
FIG. 7 depicts the % of stem cells and progenitor cells in GBM cell lines treated with LIF or BMP-4.

Leukemia Inhibitory Factor (LIF) and BMPs Reduce Stem Cell Frequency in Serially Passed Human GBM Cell Lines GBM tumor cells obtained from three different patients were serially passed in control medium (including the mitogens EGF+FGF2; see Example 6) with or without either LIF (20 ng/ml) or BMP-4 (20 ng/ml). Analysis of stem and progenitor cell frequency using the method of Example 1 revealed a significant reduction in tumor stem cell numbers by addition of LIF or BMP-4 (a statistical significance of $p<0.01$), a significant reduction in tumor progenitor cell numbers by addition of BMP-4 (a statistical significance of $p<0.05$) but no significant change in tumor progenitor cell population frequency by addition of LIF. These results indicate that BMP molecules reduce tumor stem cell and tumor progenitor cell proliferation while LIF selectively reduces tumor stem cell numbers with no effect on the tumor progenitor population. FIG. 7 depicts the results graphically (as % of untreated control values). These results indicate that LIF and BMP are each effective in reducing tNSC proliferation, even in the presence of the mitogens EGF and FGF2. This shows that LIF and/or BMP treatment will be effective in treating brain tumors in humans.

Example 11

Figure 8:
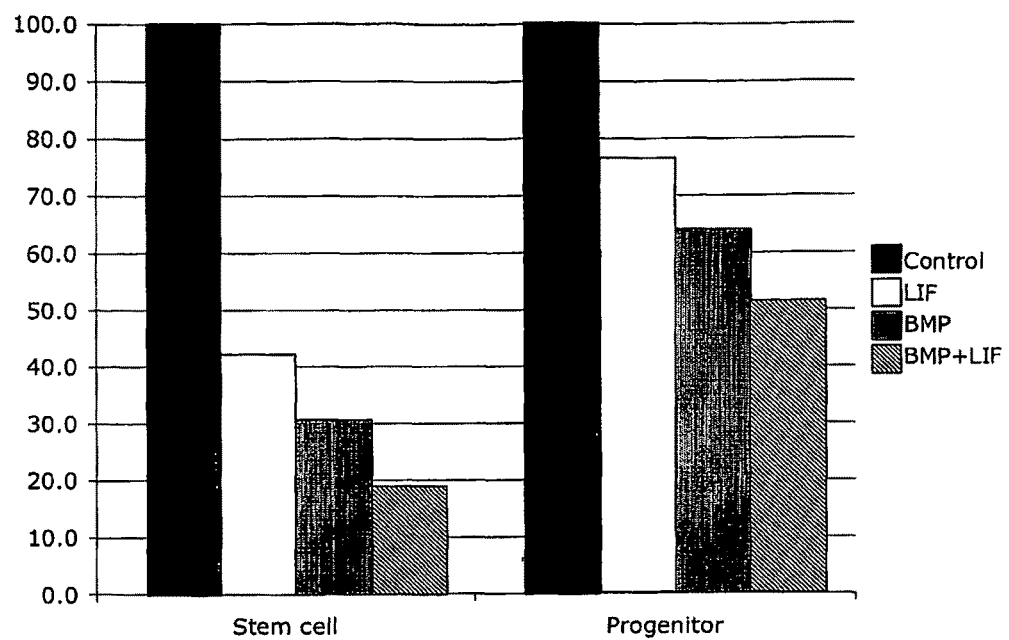
FIG. 8 depicts the % of stem cells and progenitor cells in GBM cell lines treated with LIF, BMP-4, or LIF+BMP-4.

Application of LIF and BMP-2 to Serially Passed GBM Derived Cells Reduce Stem and Progenitor Cell Frequency Serially passed GBM cells (see Example 6) in control medium (including the mitogens EGF+FGF2; see Example 6) were treated with LIF, BMP-2 or a combination of BMP-2+LIF. Control serially passed GBM cells were treated with neither protein. Growth curves were compared using the method of Example 1 to calculate stem cell and progenitor cell frequency. The data reveals a greater reduction in tumor stem cell and tumor progenitor cell frequency when LIF and BMP-2 are used together than when used alone. FIG. 8 depicts the results graphically (y-axis represents % of untreated control value). These results show that co-administration of LIF and BMP-2 is effective in reducing the proliferation of tNSCs, even in the presence of the mitogens EGF and FGF2, and that co-administration of LIF and BMP-2 will be effective in treating brain tumors in humans.

Example 12

Figure 9:
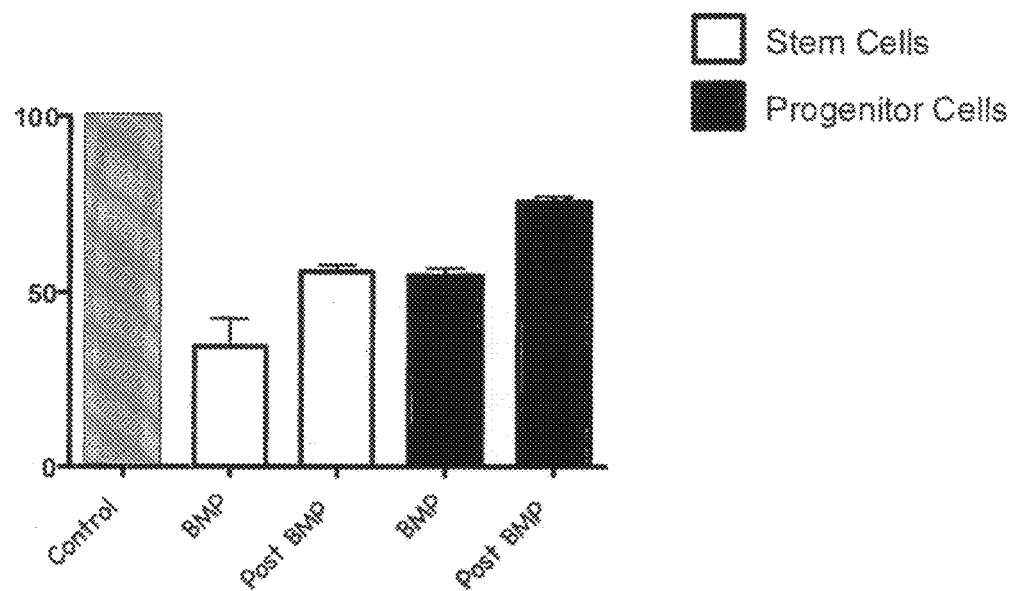
FIG. 9 depicts the % of stem cells and progenitor cells in GBM cell lines treated with BMP-2 continuously during serial passage or treated with BMP-2 transiently for one passage ("post BMP").

Transient Treatment of Cultured GBM Cells with BMP-2 Permanently Reduces Stem and Progenitor Cell Frequency GBM tumor cells obtained from three different patients were serially passed in control medium (including EGF+FGF2; see Example 6) with the addition of BMP-2 (20 ng/ml) (indicated as "BMP" in FIG. 9) or a transient exposure to BMP-2 (indicated as "post BMP" in FIG. 9) for one passage. Analysis of tumor stem cell and tumor progenitor cell frequency using the method of Example 1 revealed a significant reduction in tumor stem cell and tumor progenitor cell numbers in both BMP groups. These results indicate that a transient exposure to BMP-2 produces a permanent reduction in tumor stem cell and tumor progenitor cell frequency, even in the presence of the mitogens EGF and FGF2. These results indicate that BMP-2 treatment will have a lasting effect on brain tumor growth in humans.

Example 13

Figure 10:
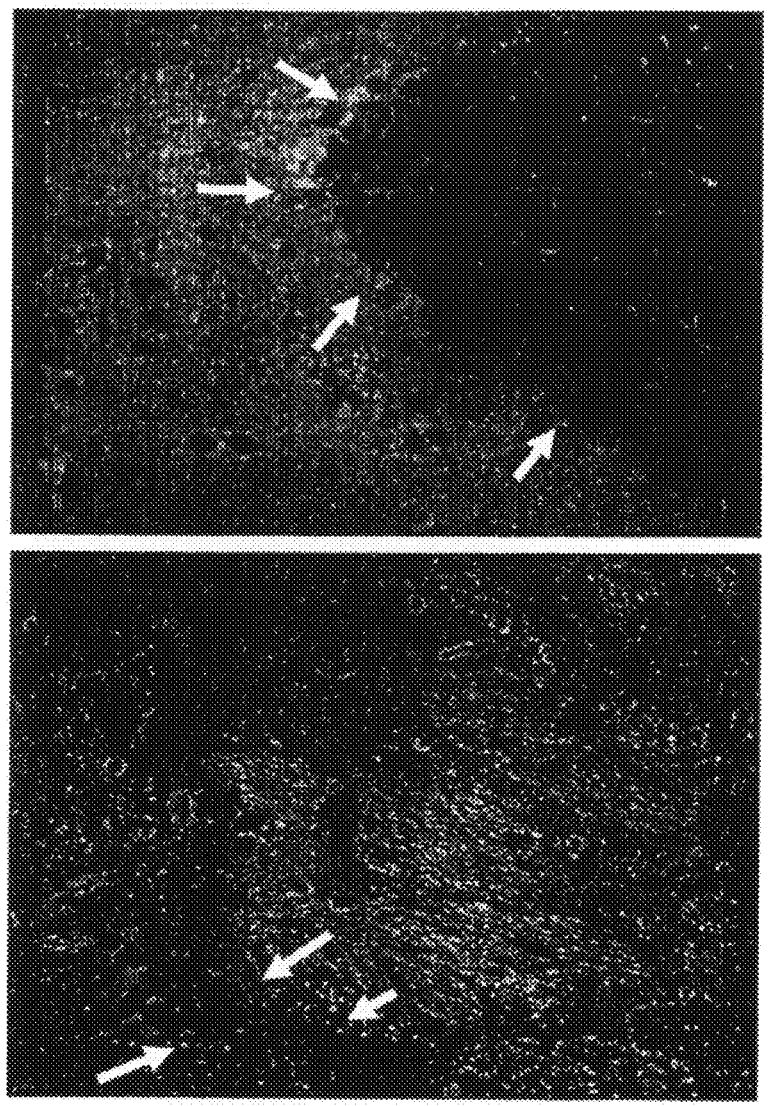
FIG. 10 illustrates GBM in immunodeficient mice caused by the transplantation of tumor neural stem cells from human GBM (top panel) and also illustrates that GBM formation is reduced when human tumor neural stem cells are pre-treated with BMP-4 or LIF prior to transplantation (lower panel).

Reduced Tumorgenicity of Cultured GBM Cells after Prior Treatment with LIF and BMP Transplantation of 100,000 tumor neural stem cells from human GBM into the brain (ventrolateral striatum) of immunodeficient mice was performed using stereotactic injection. The tumor neural stem cells established GBM in the mice. These GBM lesions became apparent as broad hyper-nucleated areas clearly distinguished by the normal tissue (see FIG. 10, top panel). When the same tumor neural stem cells were pre-treated with 100 ng/mL BMP-4 or 100 ng/mL LIF for 48 hours prior to transplantation, the formation of the tumor is enormously reduced (approximately by 80%) and the hypernucleated areas are often difficult to detect (see FIG. 10, bottom panel). These results further indicate that BMP and/or LIF treatment is effective in the treatment of human brain tumors. See also Example 22 for an additional Example.

Example 14

Assay for Tumor Stem Cell Frequency in Breast Carcinoma Tissue Following LIF and BMP-2 Treatment Tumor specimens are obtained from consenting patients undergoing biopsies for tumor resection and are enzymatically digested in a 1:1 collagenase/hyaluronidase solution for 1 hour at 37° C. followed by filtration through a 40 μm filter and plating of cells at a clonal density in serum free DMEM/F12 hormone mixture (NeuroCult, Stem Cell Technologies) with the mitogens EGF and FGF2 (20 ng/ml). After 3-5 days clonally derived clusters of cells are observed floating in suspension. These cells are collected, enzymatically dissociated and cells replated in fresh growth medium. Cell passaged in this manner every 4-7 days exhibit a geometric increase in the total numbers of cells generated.

Serial passaged mammary tumor derived stem cells are exposed to LIF and/or BMP-2 and compared to control cultures. Tumor stem cell and tumor progenitor cell frequency between the treatment and control groups is analysed by plating cells from dissociated mammary spheres in the Neural Colony Forming Cell Assay and analysing the serial growth curves with the mathematical model of Example 1.

Example 15

Assay for Tumor Stem Cell Frequency in Prostate Carcinoma Tissue Following LIF and BMP-2 Treatment Prostate cancer cells are obtained from lymph node metastasis and cultured in DMEM/F12 hormone mixture (StemCell Technologies) with the addition of 5% serum and the stem cell mitogens EGF and FGF2. Clonally derived spheroids are serially passaged following trypsinization and expansion data from passaged cells (untreated, or treated with LIF and/or BMP-2) is used to calculate tumor stem cell and tumor progenitor cell frequency using the mathematical model of Example 1.

Example 16

Assay for Tumor Stem Cell Frequency in Melanoma Tissue Following LIF and BMP-2 Treatment Melanoma cells are obtained from resected tumors and stem cells are isolated as per methods used to culture multipotent stem cells from mammalian skin (see Toma et al, Nat Cell Biol. 2001 September; 3(9):778-84, incorporated herein by reference in its entirety). Briefly, tissue is cut into small (<2 mm) pieces, washed with HEM and digested with 0.1 trypsin for 30 min at 37° C. Samples are rinsed in PBS, mechanically dissociated into a single cell suspension, filtered through a 40 um cell strainer and plated at a density of 50,000 cell per ml in Nunc T-80 tissue culture flasks. Growth medium is serum-free DMEM/F12 with hormone mix (StemCell Technologies) with the addition of the stem cell mitogens EGF and FGF2. After 7-10 divisions, clonally derived clusters of cells are identified in culture. These melanospheres are collected, dissociated into a single cell suspension and replated using fresh medium stem cell mitogens. Cultures passaged in this manner are treated with LIF or BMP-2 and the total numbers of cell generated over time is plotted on a log scale. Tumor stem cell and tumor progenitor cell frequency between the treatment and control groups is analysed using the mathematical model of Example 1.

Example 17

Treatment of Recurrent Glioblastoma Multiforme Using LIF Administration by Convection Enhanced Delivery (CED) Following Tumor Resection Patients with recurrent glioblastoma multiforme are selected. Following tumor resection, two to three catheters are placed in the brain parenchyma surrounding the resection cavity using image guidance to avoid entrance into the sulci or ventricles. Seventy-two milliliters of human LIF at 1 μg/mL is infused through the catheters over 96 hours using a syringe pump.

Example 18

Treatment of Recurrent Glioblastoma Multiforme Using BMP-4 Administration with Polymer Beads Patients with recurrent glioblastoma multiforme are selected. Following tumor resection, BMP-4 saturated polyacrylic beads (releasing BMP-4 for over a week) are implanted at the resection site.

Example 19

Expression of BMPRs in Cells from GBM Specimens

The expression of BMPs and their receptor (BMPR) transcripts and proteins in cells derived from GBM tissue were evaluated on the CD133+ tNSC population derived from GBM tissue (Singh, S. K. et al., Nature 432, 396-401 (2004)). While the in vitro data below illustrate data obtained cells from one representative GBM specimen, equivalent results were obtained with four additional samples, which include CD133+ sorted or unsorted cells, either acutely isolated from GBMs or following brief culturing with mitogens (cultured cells) (Galli et al, Cancer Res 64, 7011-21 (2004); Singh, S. K. et al., Nature 432, 396-401 (2004)). Transcripts for all three BMPR subtypes (BMPR1A, -1B, -2) and BMPs were found in both acutely dissociated and in cultured GBM cells. See FIG. 11A where lane 1 is a negative control, lane 2 is acutely dissociated GBM CD133+ cells, lane 3 is cultured GBM CD133+ cells, and lane 4 is MCF7 cells as a positive control. Also, the cognate receptor and BMP-4 proteins were found in both populations, in both CD133+ and CD133− fractions. See FIG. 11B-G which depicts immunofluorescence of the indicated proteins in freshly isolated (FIG. 11B-D) and cultured (FIG. 11E-G) CD133+ GBM cells.

BMPRs were functional, as Smad 1-5-8 phosphorylation was observed following addition of saturating concentrations of BMP-4 (100 ng/ml)—one of the most effective ligands—while no activation of the p38 MAPK pathway was ever detected. See FIG. 11H-J which shows the phosphorylation and nuclear translocation of the receptor-activated Smad proteins (antiphosphoSmad 1,5,8) at the indicated times (in minutes) in GBM cells.

Figure 11:
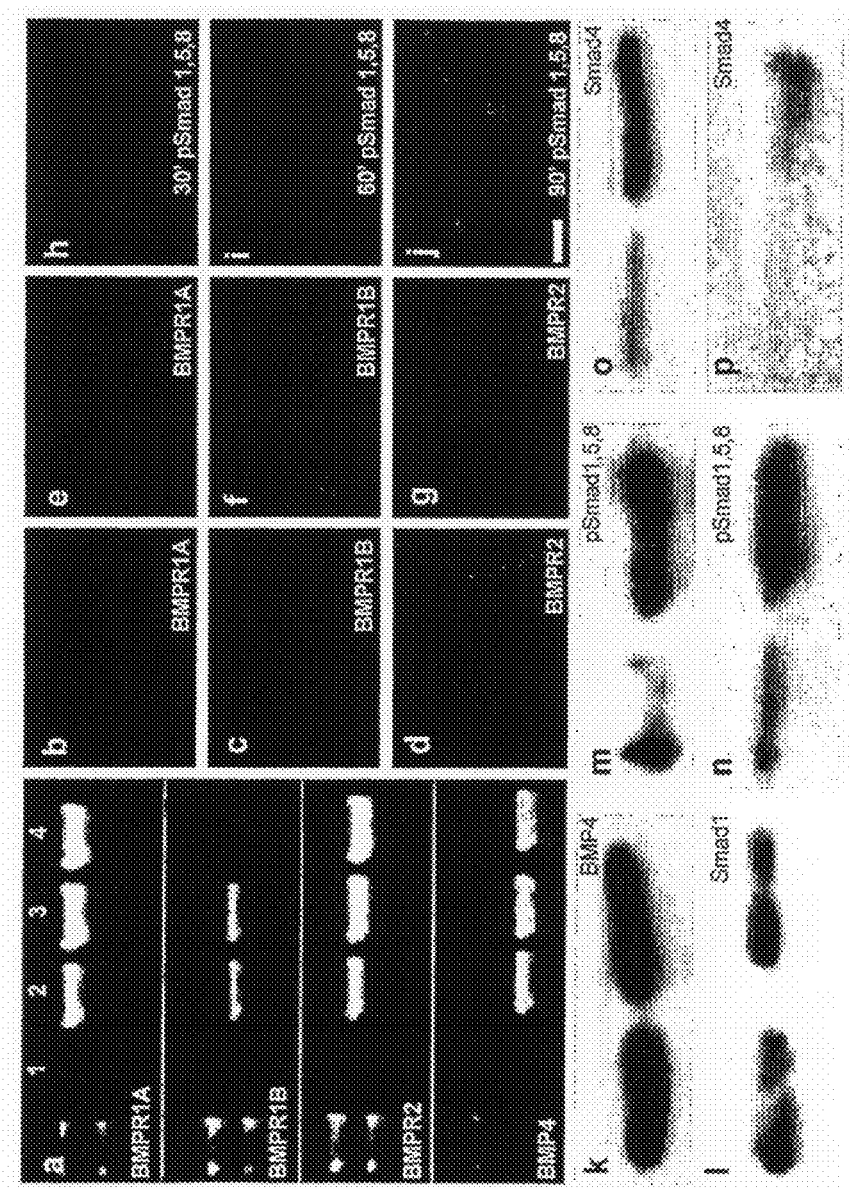
FIG. 11A depicts transcript levels for BMPR1A, BMPR1B, BMPR2, and BMP-4 for cells from acutely dissociated and cultured GBM cells.
FIG. 11B-D depicts BMPR1A, BMPR1B, and BMPR2 immunoreactivity in freshly isolated GBM cells.
FIG. 11E-G depicts BMPR1A, BMPR1B, and BMPR2 immunoreactivity in cultured GBM cells.
FIG. 11H-I depicts phosphoSmad 1,5,8 immunoreactivity in GBM cells.
FIG. 11K-P shows Western blot analysis of BMP-4, Smad1, phosphoSmad 1,5,8 and Smad 4 in GBM cells.

FIG. 11K-P shows Western blot analysis of the indicated proteins. FIG. 11K shows BMP-4 protein in acutely dissociated (left lane) and cultured CD133+ GBM cells (right lane). FIG. 11L shows that Smad1 levels were unchanged in BMP-4 treated cultured cells (left lane is control, right lane is BMP-4 treated). FIG. 11M-N shows increased Smad 1,5,8 phosphorylation in the presence of BMP-4 (left lanes controls; right lanes are BMP-4 treated) in freshly dissociated (FIG. 11M) and cultured (FIG. 11N) cells. FIG. 11O-P shows increased Smad4 expression in cultured (FIG. 11O) and acutely dissociated (FIG. 11P) GBM cells following BMP-4 treatment (control in left lanes; BMP-4 treatment in right lanes).

This result also indicates that the Smad 1,5,8 complex may also be a useful therapeutic target for the treatment of GBM. For example, therapeutic agents that increase the phosphorylation of the complex will have the same effect on tNSCs as BMP-4. The screening methods disclosed elsewhere in this disclosure may be used to obtain such therapeutic agents.

Example 20

Study of the Effect of BMP-4 Exposure on GBM tNSCs

Figure 12:
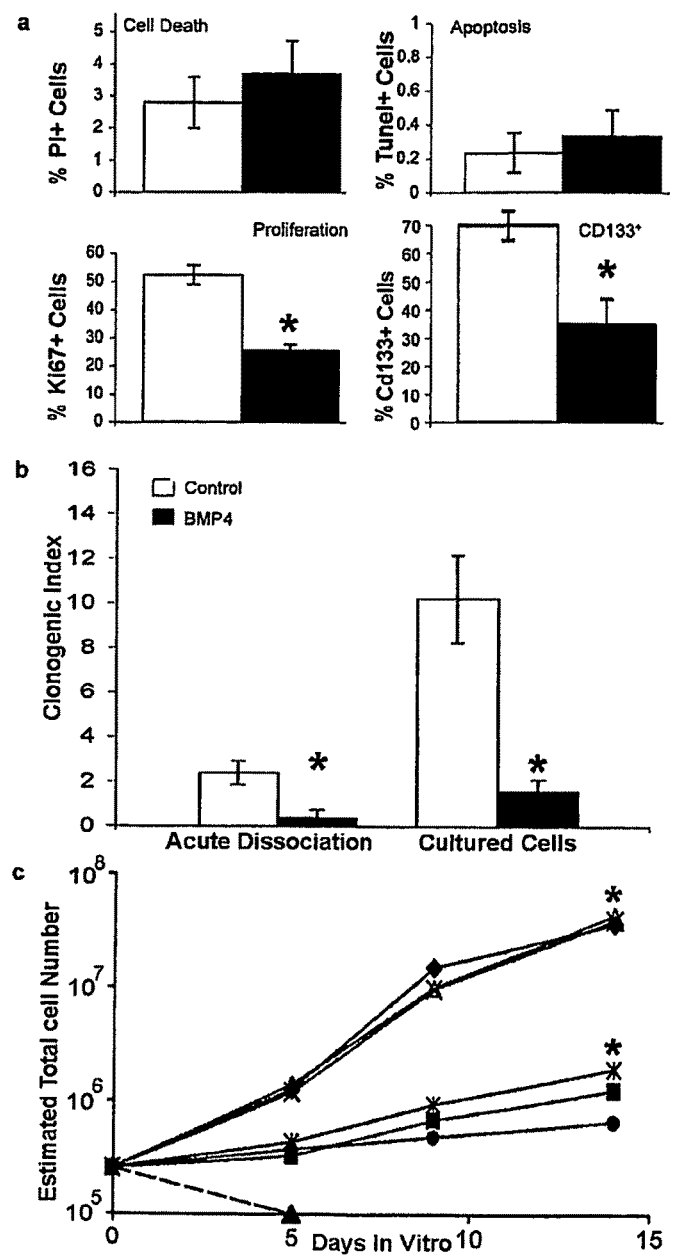
FIG. 12A depicts measurements of cell death, apoptosis, Ki67 immunoreactivity, and CD133 immunoreactivity in GBM cultures in the presence and absence of BMP-4.
FIG. 12B shows the clonogenic index of GBM cells in the presence and absence of BMP-4.
FIG. 12C depicts the propagation of GBM cells in the Neurosphere Assay in the presence and absence of BMP-4.

The nature of the effect of BMP-4 on cells isolated from GBMs was studied. Different from other cell systems (Hallahan et al, Nat Med 9, 1033-8 (2003); Zuzarte-Luis & Hurle, Semin Cell Dev Biol 16, 261-9 (2005); Hruska et al, Circ Res 97, 105-14 (2005)), including medulloblastomas (Graham et al., Mol Cell Neurosci 8, 76-83 (1996)), BMP-4 did not produce cell death (as measured by propidium iodide exclusion) or apoptosis (as measured by the TUNEL assay, but significantly reduced the proliferation (as measured by Ki67 immunofluorescence) of GBM cells in response to mitogens. FIG. 12A shows graphically the effects of BMP-4 in GBM cultures (empty columns are control cultures, black columns are BMP-4 treated; mean±SE, n=3; *p, 0.005; PI=propidium iodide).

Figure 15:
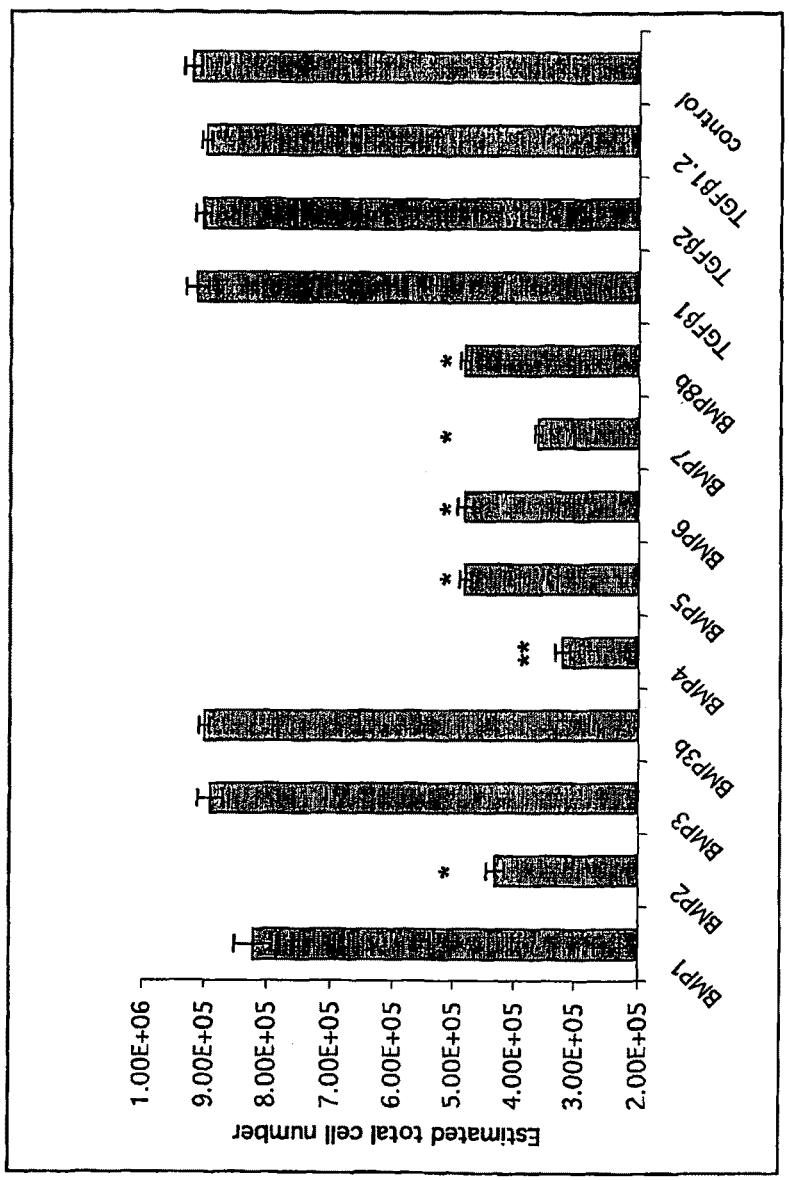
FIG. 15 depicts the effects of various BMPs on the growth of GBM cells.

The effects of other BMPs on proliferation were also assayed. See FIG. 15 which shows the effects of other BMPs (100 ng/ml) on the growth of GBM cells. BMP-2, -4, -5, -6, -7, -8b inhibit cell growth, whereas BMP1, -3 and -3b appear to be ineffective, similar to TGFβ1 and 2 and to TGFβ1.2 (a chimeric TGFβ agonist polypeptide) (all at 100 ng/ml), which were also ineffective. *p<0.005 BMPs vs control, mean±SE n=3, two-tailed Student's t-test; **p<0.001 BMP4 vs control, mean±SE n=3, two-tailed Student's t-test. Thus, BMP-2, -4, -5, -6, -7, -8b will also be useful in the methods and compositions of the disclosure, particularly for the treatment of GBM.

The anti-proliferative effect of BMP-4 was corroborated by cell cycle analysis, showing a significant increase in the number of GBM cells in G0/G1 phase and a decrease in the percentage of cells in S phase in response to BMP-4. Unlike BMP4, TGFβs—found in GBM cells (Kjellman et al., Int J Cancer 89, 251-8 (2000)), using signalling pathways overlapping with those of BMPs (Canalis et al., Endocr Rev 2, 218-35 (2003); Golestaneh et al, Oncogene 24, 5722-30 (2005)) and eliciting pro- or antimotic effects (Jennings et al., J Neurooncol 36, 123-40 (1998))—did not affect GBM cell proliferation, underlying the specificity of the BMP4 actions described here.

Two classic assays—one which determines the clonogenic index, thus measuring the percentage of clone-forming neural precursors (Gritti et al., J Neurosci 16, 1091-100 (1996); Reynolds et al., Dev Biol 175, 1-13 (1996)) and a second providing a measurement of the expansion of the size of NSC pool based on growth kinetics data (Galli et al., Development 129, 1633-44 (2002); Reynolds et al., Nat Methods 2, 333-6 (2005))—confirmed that the cytostatic effect of BMP-4 impinged upon the tNSC population in GBM cells. A 48-hour exposure to BMP-4, produced a greater than 70% reduction in the clonogenic index (% clones formed relative to total cells plated) in GBM cells, in vitro (see FIG. 12B which shows graphically the clonogenic index for control and BMP-4 treated GBM cells, both acutely dissociated and cultured; mean±SE, n=3; *p<0.005). Also, exposure of GBM cells to BMP-4 soon after isolation from the primary tumor specimen abolished their ability to undergo expansion in culture, while addition of BMP4 to GBM cells that were already expanding in vitro greatly decreased their growth rate. See FIG. 12C which depicts graphically the propagation of GBM cells in vitro using the Neurosphere Assay, revealing that cells from acutely dissociated GBM tissue could not be serially subcultured in the presence of BMP-4 (black dotted line and black solid triangle). FIG. 12C also shows that after brief expansion under the same conditions (rhombuses) cells from the same acutely dissociated tissue which were treated with BMP-4 also showed a significant reduction in the slope of their growth curve (squares). A similar effect was seen for BMP4-treated human fetal NSCs (see FIG. 12C, black stars (control) versus black circles (BMP-4)), while U87 human glioma lines (which do not bear BMPRs) were unaffected (see FIG. 12C open triangles, control versus crosses (BMP-4)).

Cytofluorimetric analysis showed that treatment with BMP4 resulted in a nearly halved size of the CD133+ population (see FIG. 12A), both in acutely dissociated and cultured GBM cells. Together, these data indicate that BMP-4 is able to target the tNSC population in GBM cells.

Figure 13:
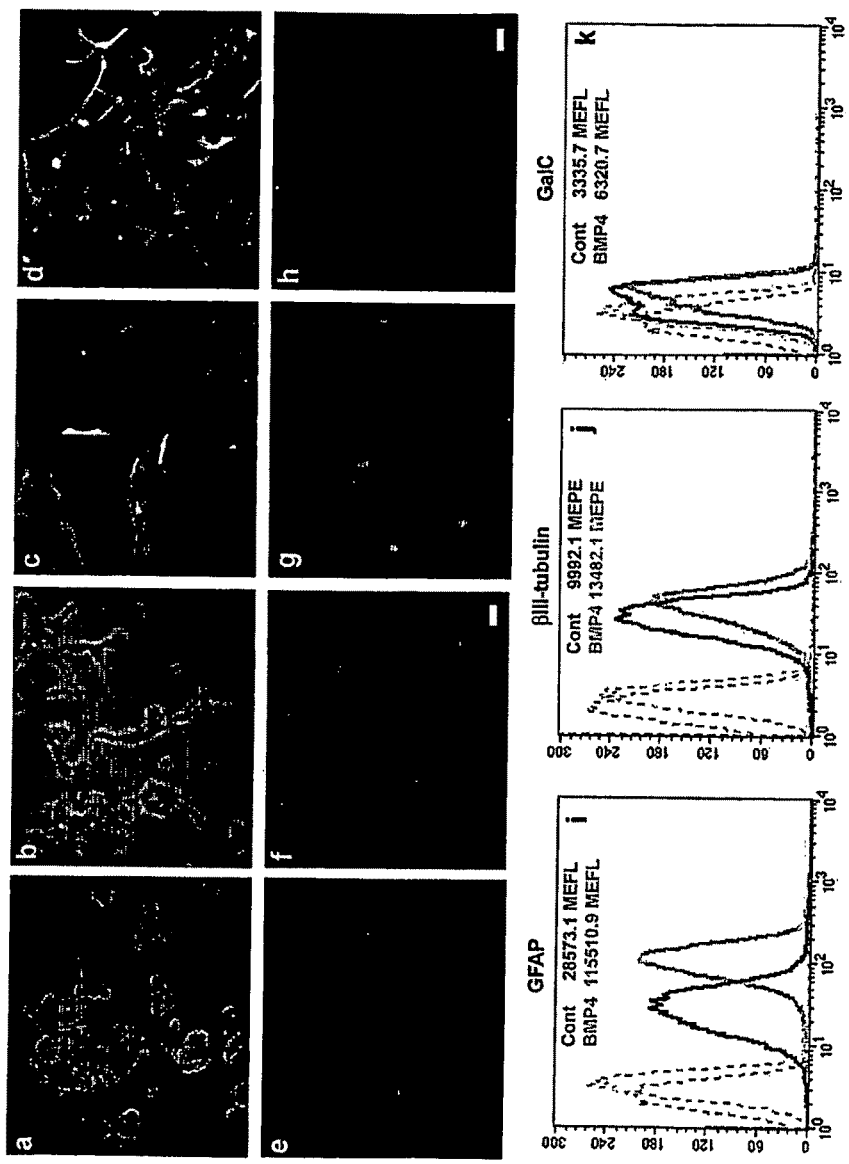
FIG. 13A depicts GBM cells in the absence of BMP-4.
FIG. 13B depicts GBM cells cultured with BMP-4.
FIG. 13C (control GBM cells) and FIG. 13D (BMP-4 treated GBM cells) show GFAP-immunoreactivity (IR)
FIG. 13E (control GBM cells) and FIG. 13F (BMP-4 treated GBM cells) show βIII-tubulin IR.
FIG. 13G (control GBM cells) and FIG. 13H (BMP-4 treated GBM cells) show GalC IR.
FIG. 13I-K shows cytofluorometric analysis of control GBM cells and BMP-4 treated GBM cells for GFAP IR, βIII-tubulin IR, and GalC IR.

Exposure of GBM cells to BMP-4 resulted in overt morphological changes, in vitro. Relative to cells grown with mitogens alone, cells receiving also BMP4 took on a more differentiated (flat, phase dark, with elaborated processes) morphology. See FIG. 13A which shows control cells and FIG. 13B which shows cells following 48 hour exposure to BMP-4. Accordingly, a considerable increase in the expression of astroglial markers (GFAP-immunoreactivity [IR]) was observed, together with a less intense augment of the labelling for neuronal (βIII-tubulin and MAPS) or oligodendroglial (GalC) markers. See FIG. 13C-H. Specifically, FIG. 13C (control) and FIG. 13D (BMP-4) show GFAP-IR; FIG. 13E (control) and FIG. 13F (BMP-4) show βIII-tubulin IR; FIG. 13G (control) and FIG. 13H (BMP-4) show GalC IR.

Quantification of the effect of BMP4 by counting the number of cells expressing specific differentiation markers, was difficult, due to the aberrant expression of neuronal and glial antigens in undifferentiated proliferating GBM cultures and within the same cell—two phenomena that are not observed in normal neural stem cells. Therefore, cytofluorimetric analysis was used to measure fluorescence signal intensity and found that, relative to control, BMP-4-treated cultures exhibited a greater than two fold increase in GFAP-IR (see FIG. 13I) and a consistent, yet not significant increase in βIII-tubulin (FIG. 13J) and GalC (FIG. 13K) immunoreactivity (MEFL=molecules of equivalent fluorescein; MEFE=molecules of equivalent phycoerthyrin).

Without being limited by theory or hypothesis, it is believed that the presently described effects of BMP-4 result either through a reduction in the numbers of symmetric divisions yielding two identical daughters that are, themselves tNSCs, or a differentiation of a fraction of the tNSCs such that they no longer are able to retain stem cell properties. Altogether, this suggests BMP-4 can override mitogenic stimulation, enforcing the acquisition of a more mature and less tumorigenic phenotype by tNSCs. This effect is unexpected because BMP-4 exerts an anti-differentiation effect on human ES cells, which increases the stem cell pool and expansion rate.

Example 21

BMP-4 Inhibits the Tumorigenic Potential of GBSCs and can be Delivered In Vivo

Both acutely dissociated and cultured CD133+ GBM cells were exposed to BMP-4 for 48 hours in culture, prior to unilateral, intrastriatal injection ($3 \times 10^5$ viable cells) in immunodeficient scid/bg mice. Tumor formation and expansion were compared to those of control animals receiving GBM cells, maintained under identical conditions, but without BMP-4.

Figure 14:
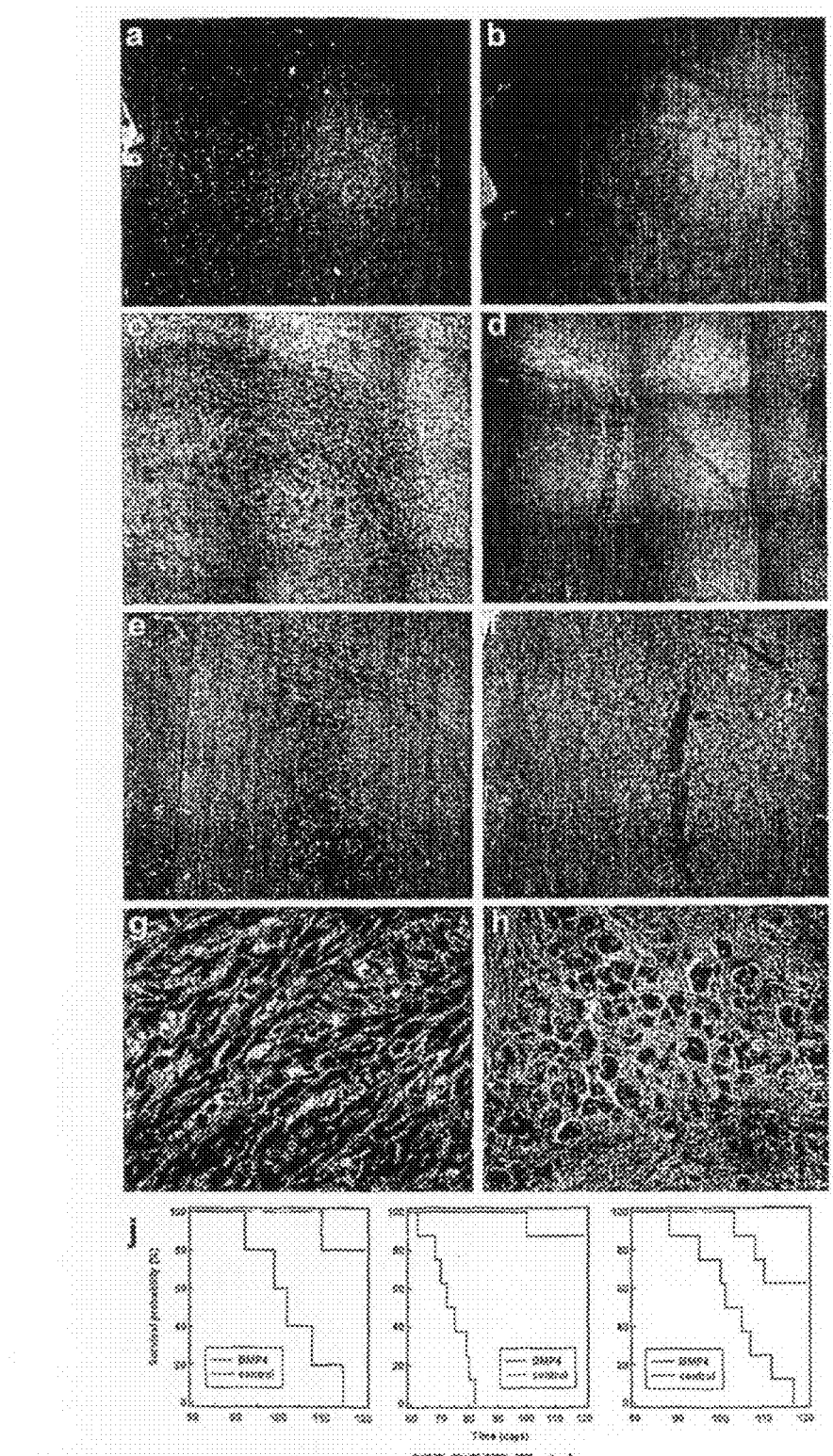
FIG. 14 E shows tumors in mice post-treated with control beads.

All animals receiving untreated GBM cells developed well-established tumor masses on the injected side (see FIG. 14A). These showed characteristic glioblastoma features, including marked nuclear atypia, expression of aberrant glial elements, extensive neovascularization and high mitotic activity (Galli et al. Cancer Res 64, 7011-21 (2004)), and invaded the lateral, third and fourth ventricles. Conversely, BMP4-treated cells did not form invasive tumors, but small, delimited lesions, which were confined to the injection site, had a low mitotic index and showed no ventricular invasion (see FIG. 14B). Between three and four months post-injection, all control animals died, whereas virtually all mice receiving BMP-4 pre-treated cells survived (see FIG. 14J which depicts survival graphically in pre- (left panel), co- (centre panel) and post-treatment (right panel) paradigms (Logrank test, p<0.001, p<0.001, and p<0.005, respectively). Identical results were observed when the residual CD133+ fraction from BMP-4-treated GBM cultures was purified by FACS and its tumorigenicity compared to that of an equal number ($1.5 \times 10^5$ CD133+ cells/animal) of CD133+ cells purified from control GBM cells. Also, as shown previously (Galli et al. Cancer Res 64, 7011-21 (2004); Singh et al., Nature 432, 396-401 (2004)), it was always possible to re-culture CD133+ tNSCs (average clonogenic frequency: 9.0±1.3% [n=2, 90 days post-transplant]) from the brain of mice receiving acutely dissociated control GBM cells. These, when re-transplanted into the brain of scid/bg mice intracerebrally, gave rise to large secondary tumors. Conversely, this was never possible when animals received BMP-4-pretreated GBM cells in the primary transplant nor was it possible to establish secondary tumors by direct injection of $3 \times 10^5$ cells, which were acutely dissociated from the primary tumors from these same mice.

Taken together, these findings demonstrate that even transient exposure to BMP-4 depletes the GBM tNSC population and produces a prominent decrease of the in vivo tumor-initiating ability of GBM cells. See also Example 13.

Example 22

In Vivo Delivery of BMP-4 Prevents Intercerebral Tumor Establishment and Growth

In vivo delivery of BMP-4 was then evaluated as a treatment to prevent intercerebral tumor establishment and growth. Transplantation of GBM was accompanied by injection of vehicle- (control) or BMP-4-saturated polyacrylic beads (releasing BMP-4 for over 1 week), at the site of cells' engraftment, either at the same time as cells (co-treatment paradigm) or ten days later (post-treatment paradigm). Histological, serial reconstruction in both treatments revealed a significant reduction in the maximal extension of the tumor mass in the BMP-4-treated animals versus controls. Specifically, in all experimental settings, animals receiving control beads developed large, malignant tumors (FIG. 14C (cultured GBM cells, 4 weeks post-injection, co-treatment paradigm); FIG. 14E (freshly isolated GBM cells, 30 days after cell injection, post-treatment paradigm) and soon died (FIG. 14J), whereas mice implanted with BMP4-releasing beads displayed small, confined lesions (FIG. 14D (cultured GBM cells, 4 weeks post-injection, co-treatment paradigm); FIG. 14F (freshly isolated GBM cells, 30 days after cell injection, post-treatment paradigm); and survived significantly longer (FIG. 14J). Control tumors contained pleiomorphic, highly neoplastic elements, with reactive chromatin and highly malignant, infiltrating cells (FIG. 14G). Conversely, BMP-4-treated animals displayed lesions embodying little neoplastic cells, many highly differentiated elements and numerous macrophages (FIG. 14H). The mitotic index was significantly higher in controls relative to BMP-4-treated animals (co-treatment: control 3.8±0.2 versus BMP-4 0.20±0.1; p<0.01. Post-treatment: control 4.3±0.3 versus BMP4 0.7±0.3; p<0.05. Mean±SE, n=4, two-tailed Student's t-test). Immunofluorescence in vivo, revealed the presence of astrocytes and nestin-positive cells, but not oligodendroglial or neuronal cells, in both control and BMP4-treated tumors.

These results indicate that intracerebral implantation of a device that releases or otherwise delivers BMP-4 will be effective in the treatment of GBM in humans.

Example 23

Neutralizing BMP-4 Antibody Studies

Example 19 shows that endogenous BMP4 and other BMPs are found in GBM cells. In agreement with the findings presented in the foregoing Examples, neutralizing anti-BMP4 antibodies increase tNSC proliferation. This suggests that endogenous BMPs may act physiologically on GBM cells in vivo, though their effects are insufficient to halt tumor growth. Studying the mechanisms behind this phenomenon, for example the possible presence of endogenous BMP antagonists in the tumor (Canalis et al., Endocr Rev 2, 218-35 (2003)), might point to alternative strategies for the cure of GBMs. Also, BMPs, their cognate receptors and their associated intracellular transduction mechanisms, particularly the Smad pathway, emerge as promising target for therapies aiming more specifically at the cells mainly responsible for GBM establishment and expansion.

Example 24

Primary Culture, Culture Propagation, Cloning and Cell Line Establishment

GBM cells were obtained by processing tumor samples as described by Galli et al., Cancer Research (2004) 64: 7011-7021. Acutely dissociated cells were sorted for their immunoreactivity to CD133 (see below) and plated in 25 cm$^2$ tissue culture flasks at a final density of 2500-cells/cm$^2$ in NeuroCult® NS-A serum-free medium (Stem Cell Technologies). Culture propagation, clonogenic assay and population analysis were performed using the same conditions described previously Galli et al., Development 129, 1633-44 (2002). For pre-treatment of acutely dissociated CD133+ GBM cells with BMP4, these were plated in the same medium devoid of mitogens (control) or containing 100 ng/ml of BMP4 for 48 hours prior to transplantation.

Example 25

Immunocytochemistry $2.5 \times 10^4$ cells/cm$^2$ GBM cells were plated onto Matrigel-coated glass coverslips in the presence of FGF2/EGF and treated with BMP4 (100 ng/ml) for 48 h. Cells were then washed and fixed in 4% paraformaldehyde (10 minutes). Multiple immunofluorescence for neural antigens (GFAP, Dako Corporation; Tuj1, Babco; Galc, Chemicon) was performed as described by Galli et al., Cancer Research (2004) 64: 7011-7021. Ki67 staining (1:1000, NovoCastra, Newcastle, UK) detected proliferating cells.

After fixation in 4% paraformaldehyde, immunostaining for BMPR-1A, -1B and -2 was carried out according to the manufacturer's instructions (1:50 R&D Systems). When staining for phospho-Smad 1 (1:100 Cell Signaling, Beverly, Mass.) cells were treated with BMP-4 (100 ng/ml) at different times (from 5 minutes to 2 hours). Appropriate isotypic or negative controls were always included throughout these procedures. Apoptotic cells were detected using digoxigenin-based modification of the original TUNEL method introduced by Gavrieli et al., J Cell Biol 119, 493-501 (1992) using the fluorescein-dUTP TUNEL assay (In Situ Cell Death Detection Kit, Fluorescein, Roche Applied Science). Briefly, cells grown on 12-mm coverslips were fixed in 4% paraformaldehyde for 10 min at room temperature and then rinsed in PBS. Cells were then permeabilized for 2 min on ice before labeling with 50 ul of TUNEL reaction mixture and incubating at 37° C. for 1 hour in a humidified chamber under parafilm coverslips. After washing with PBS, slides were mounted in DAN-containing Vectashield™ and examined by fluorescence microscopy. For propidium iodide (PI) staining, cells were fixed in 4% paraformaldehyde for 10 min at room temperature, rinsed in PBS and incubated with PI (1 ug/ml) for 5 min at room temperature: After washing, coverslips were mounted in DAPI-containing Vectashield™ and analysed by fluorescence microscopy. PI exclusion denoted viable cells. For the assays in Example 19, samples were run in six replicates for each condition tested.

Example 26

Conventional and Real-Time PCR

Total RNA was isolated from cultured and acutely dissociated GBM cells using TRIzol reagent (Life Technologies, Rockville, Md.), and reverse-transcribed using SuperScript RNAse H-Reverse Transcriptase (Life Technologies). The amounts of cDNA used as templates in the conventional PCR reactions were normalized with reference to glyceraldehyde-3-phosphate dehydrogenase (GAPDH). MCF-7 cell lines were used as positive controls for BMPRs. PCR products were visualized by electrophoresis in agarose (1%) gels stained with ethidium bromide.

Quantitative RT-PCR reactions were run in triplicate using Brilliant® SYBR® Green QPCR Core Reagent Kit (Stratagene, La Jolla, Calif.). SYBR Green dye binds to any PCR product, and therefore does not require the use of sequence-specific probes. Fluorescent emission was recorded in real-time (Chromo 4 Four-Color Real-Time PCR Detector, MJ Research, Bio-Rad). Gene expression profiling was completed using the comparative Ct method of relative quantification. Relative RNA quantities were normalized to two endogenous controls, GAPDH and 18S ribosomal RNA (18S rRNA).

For conventional PCR, the following primers were used: BMP4, forward: 5'-cttcagtctggggaggag-3' SEQ ID NO:13, reverse: 5'-gatgaggtgcccaggcac-3' SEQ ID NO:14; BMPR1A, forward: 5'-aatggagtaaccttagcaccagag-3' SEQ ID NO:15, reverse: 5'-agctgagtccaggaacctgtac-3' SEQ ID NO:16; BMPR1B, forward: 5'-ggttgcctgtggtcacttctgg-3' SEQ ID NO:17, reverse: 5'-tagtctgtgattaggtacaactgg-3' SEQ ID NO:18; BMPR2, forward: 5'-tcagatatatggcaccagaagtg-3' SEQ ID NO:19, reverse: 5'-gtggagaggctggtgacacttg-3' SEQ ID NO:20; GAPDH, forward: 5'-cggagtcaacggatttggtcgtat-3' SEQ ID NO:21, reverse: 5'-agccttctccatggtggtgaagac-3' SEQ ID NO:22. PCR amplification conditions consisted of 35 cycles with primers annealing at 56° C.

For RT-PCR, the following primers were used: BMPR1A, forward: 5'-caggttcctggactcagctc-3' SEQ ID NO:23, reverse: 5'-ctttccttgggtgccataaa-3' SEQ ID NO:24; BMPR1B, forward: 5'-aaaggtcgctatggggaagt-3' SEQ ID NO:25, reverse: 5'-gcagcaatgaaacccaaaat-3' SEQ ID NO:26; BMPR2, forward: 5'-gctaaaatttggcagcaagc-3' SEQ ID NO:27, reverse: 5'-cttgggccctatgtgtcact-3' SEQ ID NO:28; GAPDH: the same primers as described for conventional PCR were used; 18S rRNA, forward: 5'-agtccctgcccttgtacaca-3' SEQ ID NO:29, reverse: 5'-gatccgagggcctcactaaac-3' SEQ ID NO:30. The specificity of the primers was confirmed for every PCR run by dissociation curve analysis (Opticon®2 and Chromo4™ Real-Time System Software, MJ Research). RT-PCR amplification conditions consisted of 40 cycles with primers annealing at 56° C.

Example 27

Western Blotting

Proteins were harvested by washing cultured and acutely dissociated GBM cells in cold PBS and lysing with 500 μl of 1× Sample Buffer (62.5 mM Tris HCl, pH 6.8 at 25° C.; 2% w/v SDS; 10% Glycerol; 50 mM DTT; 0.01% w/v Bromophenol Blue). Samples were incubated on ice and stored at −20° C. Aliquots were boiled for 5 minutes, incubated on ice and loaded 20 μl/lane onto SDS-PAGE gel (10 cm×10 cm). Proteins were then transferred to nitrocellulose membranes. Membranes were blocked in 5% milk powder/0.1% Tween in TBS for 1 h at room temperature and washed 3 times with 15 ml of TBS/0.1% Tween. Blots were then incubated with anti-Smad1-5-8 (1:1000; Cell Signaling), anti-phospho Smad1-5-8 (1:1000; Cell Signaling), anti-Smad4 (1:200; Santa Cruz), anti-BMP4 (1:400, Chemicon) in 5% milk powder/0.1% Tween in TBS. For all blots, membranes were washed 3 times with 15 ml of TBS/0.1% Tween and then incubated with the appropriate horseradish conjugated secondary antibody (1:1000, Amersham) in 5% milk powder/0.1% Tween in TBS for 1 hour at room temperature. Bands were visualised by chemiluminescence (ECL; Amersham).

Example 28

Flow Cytometry

To determine the phosphorylation status of p38 and Smad 1-5-8, cell preparations were centrifuged and resuspended in 0.5 ml PBS and 0.5 ml 4% paraformaldehyde for 10 min at 37° C. GBM cells were then permeabilized by slowly adding ice-cold 100% methanol to pre-chilled cells while gently vortexing, giving a final concentration of 90% methanol. Following incubation for 30 min at 4° C. and centrifugation, the cells were washed twice with 3 ml of 0.5% bovine serum albumin (BSA, Sigma) in PBS, resuspended in 150 ul PBS and incubated for 10 min at room temperature. After incubation, they were exposed to a 1:50 dilution of anti-phospho Smad 1-5-8 rabbit polyclonal antibody (Cell Signaling) or 1:50 of phospho-p38 MAP kinase rabbit polyclonal antibody (Cell Signaling) for 1 hour in the dark at room temperature. After extensive washes, a 1:800 dilution of goat anti-rabbit Ig FITC-labeled antibody (BD, Pharmingen) was added and each tube was incubated for 30 min in the dark at room temperature. After two washes with 3 ml of 0.5% BSA (Sigma) in PBS cells were resuspended in 0.5 ml PBS and analysed by flow cytometry. Autofluorescence and isotype controls were run routinely for all of these assays.

For cell cycle analysis, 1 million cultured and acutely dissociated GBM cells/sample were treated with BMP4 (100 ng/ml) for the indicated time. GBM cells were then resuspended in equal volumes of ice-cold PBS and 100% ethanol, and incubated on ice for 30 minutes. After centrifugation, the cell pellet was washed 3× with PBS and centrifuged for 5 minutes. GBM cells were then incubated overnight in the dark in 1 ml PBS containing RNAse (12.5 ug/ml; Sigma) and propidium iodide (3 ug/ml; Sigma) and analysed by flow cytometry.

For quantification of CD133 expression, double-staining flow cytometry was performed, using 7-amino actinomycin D (7AAD) to identify viable cells. After washing in PBS, GBM cells were resuspended in 7AAD labeling buffer (0.1 M phosphate-citrate buffer containing 0.15 M NaCl, 5 mM EDTA, 0.5% BSA and 0.004% saponin, pH 6.0) before 7AAD was added in a final concentration of 20 uM as described by Toba et al., Immunol Methods 182, 193-207 (1995). Following 7AAD incubation for 5-7 min, GBM cells were incubated with monoclonal CD133/1 (CD133)-PE conjugate antibody (1:40, Miltenyi Biotec) for 30 min at 4° C. and washed with 1 ml of growth medium. Cells were then centrifuged at 500×g for 5 min, resuspended in 0.5 ml growth medium and analysed by flow cytometry. The same analysis was also performed using another monoclonal CD133/2 (293C3)-PE conjugate antibody, yielding identical results.

GBM cell sorting (MoFlo High Performance Cell Sorter, DakoCytomation) was performed using the same dilution of CD133/1 (CD133)-PE conjugate and CD133/2 (293C3)-PE conjugate antibodies. As described by Singh et al. (Nature (2004) 432:396-401), sorted cells were analysed for purity by flow cytometry with a FACSCalibur machine (BD Biosciences) using the same antibodies. Purity was at least 87% for both positive and negative CD133 fractions.

For glial fibrillary acidic protein (GFAP), βIII-tubulin, and galactocerebroside C (GalC, also sometimes referred to as "GC") quantification, a rainbow calibration particle mixture (8 peaks), 3.0-3.4 um (BD Biosciences) was used for calibration, and the intensity of cell labeling was expressed as molecules of equivalent phycoerythrin (MEPE) or molecules of equivalent fluorescein (MEFL). Briefly, for intracellular staining cells were permeabilized by in 0.5 ml of Cytofix/Cytoperm solution (BD Biosciences) at room temperature for 20 min. Cells were washed with 2 ml of BD Perm/Wash 1× (BD Biosciences) and incubated at room temperature for 10 min. After centrifugation, they were resuspended in 0.2 ml BD Perm/Wash solution 1× (BD Biosciences) containing the appropriate primary antibody mix. For membrane antigens, cells were resuspended in 0.2 ml of growth medium and then incubated for 30 min at 4° C. with the following primary antibodies: 1:400 polyclonal anti-GFAP (Dako Corporation), monoclonal anti-βIII-tubulin (Babco), and monoclonal anti-galC (Chemicon). The cells were then washed and exposed for 30 min at 4° C. to secondary antibody. In the case of intracellular antigens these were 1:800 goat anti-rabbit Ig FITC-labeled or goat anti-mouse IgG R-PE-labeled antibody (BD, Pharmingen), while for membrane antigens 1:1000 FITC-conjugated F(ab')2 goat anti-mouse IgM or FITC-conjugated goat anti-mouse IgM (Jackson ImmunoResearch) were used. After extensive washing, cells were resuspended and analysed by flow cytometry.

For all the above assays, analyses were performed by flow cytometry (FACSCalibur, BD Biosciences) using CellQuest software (BD Biosciences). Background fluorescence was estimated by substituting the specific primary antibodies with specific isotype controls. Measurement of autofluorescence was also routinely conducted for each condition tested.

Example 29

Evaluation of Tumorigenicity by Orthotopic Injection and Immunohistochemistry

Tumorigenicity was determined by orthotopic transplantation of GBM cells either grown under control conditions or with the further addition of 100 ng/ml of BMP-4 for 48 hours. Prior to transplantation, cells were washed and resuspended in PBS ($10^8$ cells/ml). Three microliters were injected stereotactically into the right striatum of immunodeficient mice as described previously in Galli et al., Cancer Research (2004) 64: 7011-7021. Polymer-based delivery of BMP-4 was performed using BMP-4-loaded heparin acrylic beads (100 beads/animal; Sigma-Aldrich). Prior to transplantation, beads were incubated for 1 hour at 37° C. in PBS alone or containing 0.65 μg/μl of BMP4 and thoroughly rinsed 2×3 times with PBS prior to implantation. Hematoxylin and eosin staining and immunohistochemistry were performed on paraffin-embedded, 4 urn-thick mycrotome sections, processed as described previously Galli et al., Cancer Res 64, 7011-21 (2004).

A downward sloping plot of the cumulative chance (y-axis) of surviving during time periods (x-axis) was performed using the software MedCalc (Mariakerke, Belgium). Significant differences in survival were determined by the Logrank test.

What is claimed is:

1. A method for reducing a tumor-initiating cell pool comprising a tumor stem cell and a tumor progenitor cell of a glioblastoma multiforme brain tumor in a subject, the method comprising administering to the subject a pharmaceutical composition comprising a therapeutic amount of a Bone Morphogenetic Protein 4 (BMP-4) preparation, the therapeutic amount of the BMP-4 preparation being effective to reduce the tumor-initiating cell pool of the tumor stem cell or the tumor progenitor cell by irreversibly reducing (1) size of the tumor stem cells or the tumor progenitor cells; (2) clonogenic index of the tumor stem cells or the tumor progenitor cells; (3) growth rate of the tumor stem cells or the tumor progenitor cells; or (4) a combination thereof, wherein the administering is to an unresected tumor, to a resection cavity following tumor resection, or first intratumorally and then to the resection cavity.

2. The method of claim 1, wherein the BMP-4 preparation comprises full length human BMP-4 or a fragment of the full length human BMP-4.

3. The method according to claim 1, wherein the therapeutic amount of the BMP-4 preparation is effective to increase Bone Morphogenetic Protein Receptor (BMPR)-mediated signaling in the tumor stem cell or the tumor progenitor cell.

4. The method of claim 3, wherein the increase in BMPR mediated signaling in the tumor stem cell or the tumor progenitor cell modulates at least one tumor stem cell or tumor progenitor cell characteristic selected from the group consisting of cell survival, self-renewal, symmetric division, proliferation, and differentiation properties.

5. The method according to claim 3, wherein the therapeutic amount of the BMP-4 preparation is effective to decrease a quantity of the tumor stem cell or the tumor progenitor cell in the tumor.

6. The method according to claim 3, wherein the therapeutic amount of the BMP-4 preparation is effective to reduce growth of the tumor.

7. The method according to claim 1, wherein the therapeutic amount of the BMP-4 preparation is associated with at least one polymeric wafer or at least one polymeric bead.

8. The method according to claim 1, wherein the therapeutic amount of the BMP-4 preparation is effective to reduce likelihood that the tumor stem cell or the tumor progenitor cell undergoes a symmetrical division.

9. The method according to claim 7, wherein the therapeutic amount of the BMP-4 preparation is effective to increase Bone Morphogenetic Protein Receptor (BMPR)-mediated signaling in the tumor stem cell or the tumor progenitor cell.

10. The method according to claim 1, wherein the therapeutic amount of the BMP-4 preparation is effective to induce differentiation of the tumor stem cell or the tumor progenitor cell in the tumor.

11. The method according to claim 1, wherein when combined with surgery, the glioblastoma multiforme brain tumor is at least partially resected to form a resection cavity into which said Bone Morphogenetic Protein-4 (BMP-4) preparation is released.

12. The method according to claim 1, wherein the method is combined with at least one of chemotherapy, radiotherapeutics or radiotherapy, and surgery.

13. The method according to claim 1, wherein the pharmaceutical composition further comprises a therapeutic amount of temozolimide.

* * * * *

SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: RT-PCR primer sequence 5' 3' hBMPR-1A Fw -continued

<400> SEQUENCE: 1
aatggagtaa ccttagcacc agag                                            24

<210> SEQ ID NO 2
<211> LENGTH: 22
<212> TYPE: DNA
<213> ORGANISM: Artificial Sequence
<220> FEATURE:
<223> OTHER INFORMATION: RT-PCR primer sequence 5' 3' hBMPR-1A Rw

<400> SEQUENCE: 2
agctgagtcc aggaacctgt ac                                              22

<210> SEQ ID NO 3
<211> LENGTH: 22
<212> TYPE: DNA
<213> ORGANISM: Artificial Sequence
<220> FEATURE:
<223> OTHER INFORMATION: RT-PCR primer sequence 5' 3' hBMPR-1B Fw

<400> SEQUENCE: 3
ggttgcctgt ggtcacttct gg                                              22

<210> SEQ ID NO 4
<211> LENGTH: 24
<212> TYPE: DNA
<213> ORGANISM: Artificial Sequence
<220> FEATURE:
<223> OTHER INFORMATION: RT-PCR primer sequence 5' 3' hBMPR-1B Rw

<400> SEQUENCE: 4
tagtctgtga ttaggtacaa ctgg                                            24

<210> SEQ ID NO 5
<211> LENGTH: 23
<212> TYPE: DNA
<213> ORGANISM: Artificial Sequence
<220> FEATURE:
<223> OTHER INFORMATION: RT-PCR primer sequence 5' 3' hBMPR-2 Fw

<400> SEQUENCE: 5
tcagatatat ggcaccagaa gtg                                             23

<210> SEQ ID NO 6
<211> LENGTH: 22
<212> TYPE: DNA
<213> ORGANISM: Artificial Sequence
<220> FEATURE:
<223> OTHER INFORMATION: RT-PCR primer sequence 5' 3' hBMPR-2 Rw

<400> SEQUENCE: 6
gtggagaggc tggtgacact tg                                              22

<210> SEQ ID NO 7
<211> LENGTH: 20
<212> TYPE: DNA
<213> ORGANISM: Artificial Sequence
<220> FEATURE:
<223> OTHER INFORMATION: Real Time PCR primer sequence 5' 3' hBMPR1a Fw

<400> SEQUENCE: 7
caggttcctg gactcagctc                                                 20

<210> SEQ ID NO 8

```
<211> LENGTH: 20
<212> TYPE: DNA
<213> ORGANISM: Artificial Sequence
<220> FEATURE:
<223> OTHER INFORMATION: Real Time PCR primer sequence 5' 3' hBMPR1a Rw

<400> SEQUENCE: 8
ctttccttgg gtgccataaa                                               20

<210> SEQ ID NO 9
<211> LENGTH: 20
<212> TYPE: DNA
<213> ORGANISM: Artificial Sequence
<220> FEATURE:
<223> OTHER INFORMATION: Real Time PCR primer sequence 5' 3' hBMPR1b Fw

<400> SEQUENCE: 9
aaaggtcgct atggggaagt                                               20

<210> SEQ ID NO 10
<211> LENGTH: 20
<212> TYPE: DNA
<213> ORGANISM: Artificial Sequence
<220> FEATURE:
<223> OTHER INFORMATION: Real Time PCR primer sequence 5' 3' hBMPR1b Rw

<400> SEQUENCE: 10
gcagcaatga aacccaaaat                                               20

<210> SEQ ID NO 11
<211> LENGTH: 20
<212> TYPE: DNA
<213> ORGANISM: Artificial Sequence
<220> FEATURE:
<223> OTHER INFORMATION: Real Time PCR primer sequence 5' 3' hBMPR2 Fw

<400> SEQUENCE: 11
gctaaaattt ggcagcaagc                                               20

<210> SEQ ID NO 12
<211> LENGTH: 20
<212> TYPE: DNA
<213> ORGANISM: Artificial Sequence
<220> FEATURE:
<223> OTHER INFORMATION: Real Time PCR primer sequence 5' 3' hBMPR2 Rw

<400> SEQUENCE: 12
cttgggccct atgtgtcact                                               20

<210> SEQ ID NO 13
<211> LENGTH: 18
<212> TYPE: DNA
<213> ORGANISM: Artificial Sequence
<220> FEATURE:
<223> OTHER INFORMATION: Conventional PCR primer sequence 5' 3' BMP4 Fw

<400> SEQUENCE: 13
cttcagtctg gggaggag                                                 18

<210> SEQ ID NO 14
<211> LENGTH: 18
<212> TYPE: DNA
<213> ORGANISM: Artificial Sequence
<220> FEATURE:
<223> OTHER INFORMATION: Conventional PCR primer sequence 5' 3' BMP4 Rw

<400> SEQUENCE: 14
```
gatgaggtgc ccaggcac                                                    18

<210> SEQ ID NO 15
<211> LENGTH: 24
<212> TYPE: DNA
<213> ORGANISM: Artificial Sequence
<220> FEATURE:
<223> OTHER INFORMATION: Conventional PCR primer sequence 5' 3' BMPR1A
      Fw

<400> SEQUENCE: 15
aatggagtaa ccttagcacc agag                                             24

<210> SEQ ID NO 16
<211> LENGTH: 22
<212> TYPE: DNA
<213> ORGANISM: Artificial Sequence
<220> FEATURE:
<223> OTHER INFORMATION: Conventional PCR primer sequence 5' 3' BMPR1A
      Rw

<400> SEQUENCE: 16
agctgagtcc aggaacctgt ac                                               22

<210> SEQ ID NO 17
<211> LENGTH: 22
<212> TYPE: DNA
<213> ORGANISM: Artificial Sequence
<220> FEATURE:
<223> OTHER INFORMATION: Conventional PCR primer sequence 5' 3' BMPR1B
      Fw

<400> SEQUENCE: 17
ggttgcctgt ggtcacttct gg                                               22

<210> SEQ ID NO 18
<211> LENGTH: 24
<212> TYPE: DNA
<213> ORGANISM: Artificial Sequence
<220> FEATURE:
<223> OTHER INFORMATION: Conventional PCR primer sequence 5' 3' BMPR1B
      Rw

<400> SEQUENCE: 18
tagtctgtga ttaggtacaa ctgg                                             24

<210> SEQ ID NO 19
<211> LENGTH: 23
<212> TYPE: DNA
<213> ORGANISM: Artificial Sequence
<220> FEATURE:
<223> OTHER INFORMATION: Conventional PCR primer sequence 5' 3' BMPR2 Fw

<400> SEQUENCE: 19
tcagatatat ggcaccagaa gtg                                              23

<210> SEQ ID NO 20
<211> LENGTH: 22
<212> TYPE: DNA
<213> ORGANISM: Artificial Sequence
<220> FEATURE:
<223> OTHER INFORMATION: Conventional PCR primer sequence 5' 3' BMPR2 Rw

<400> SEQUENCE: 20
gtggagaggc tggtgacact tg                                               22

<210> SEQ ID NO 21
<211> LENGTH: 24
<212> TYPE: DNA
<213> ORGANISM: Artificial Sequence
<220> FEATURE:
<223> OTHER INFORMATION: Conventional PCR primer sequence 5' 3' GAPDH Fw

<400> SEQUENCE: 21
cggagtcaac ggatttggtc gtat                                          24

<210> SEQ ID NO 22
<211> LENGTH: 24
<212> TYPE: DNA
<213> ORGANISM: Artificial Sequence
<220> FEATURE:
<223> OTHER INFORMATION: Conventional PCR primer sequence 5' 3' GAPDH Rw

<400> SEQUENCE: 22
agccttctcc atggtggtga agac                                          24

<210> SEQ ID NO 23
<211> LENGTH: 20
<212> TYPE: DNA
<213> ORGANISM: Artificial Sequence
<220> FEATURE:
<223> OTHER INFORMATION: RT-PCR primer sequence 5' 3' BMPR1A Fw

<400> SEQUENCE: 23
caggttcctg gactcagctc                                               20

<210> SEQ ID NO 24
<211> LENGTH: 20
<212> TYPE: DNA
<213> ORGANISM: Artificial Sequence
<220> FEATURE:
<223> OTHER INFORMATION: RT-PCR primer sequence 5' 3' BMPR1A Rw

<400> SEQUENCE: 24
ctttccttgg gtgccataaa                                               20

<210> SEQ ID NO 25
<211> LENGTH: 20
<212> TYPE: DNA
<213> ORGANISM: Artificial Sequence
<220> FEATURE:
<223> OTHER INFORMATION: RT-PCR primer sequence 5' 3' BMPR1B Fw

<400> SEQUENCE: 25
aaaggtcgct atggggaagt                                               20

<210> SEQ ID NO 26
<211> LENGTH: 20
<212> TYPE: DNA
<213> ORGANISM: Artificial Sequence
<220> FEATURE:
<223> OTHER INFORMATION: RT-PCR primer sequence 5' 3' BMPR1B Rw

<400> SEQUENCE: 26
gcagcaatga acccaaaat                                                20

<210> SEQ ID NO 27
<211> LENGTH: 20
<212> TYPE: DNA
<213> ORGANISM: Artificial Sequence
<220> FEATURE:
<223> OTHER INFORMATION: RT-PCR primer sequence 5' 3' BMPR2 Fw

```
<400> SEQUENCE: 27
gctaaaattt ggcagcaagc                                              20

<210> SEQ ID NO 28
<211> LENGTH: 20
<212> TYPE: DNA
<213> ORGANISM: Artificial Sequence
<220> FEATURE:
<223> OTHER INFORMATION: RT-PCR primer sequence 5' 3' BMPR2 Rw

<400> SEQUENCE: 28
cttgggccct atgtgtcact                                              20

<210> SEQ ID NO 29
<211> LENGTH: 21
<212> TYPE: DNA
<213> ORGANISM: Artificial Sequence
<220> FEATURE:
<223> OTHER INFORMATION: RT-PCR primer sequence 5' 3' 18S rRNA Fw

<400> SEQUENCE: 29
agtccctgcc ctttgtacac a                                            21

<210> SEQ ID NO 30
<211> LENGTH: 21
<212> TYPE: DNA
<213> ORGANISM: Artificial Sequence
<220> FEATURE:
<223> OTHER INFORMATION: RT-PCR primer sequence 5' 3' 18S rRNA Rw

<400> SEQUENCE: 30
gatccgaggg cctcactaaa c                                            21
```